United States Patent
Jones et al.

(10) Patent No.: US 7,202,091 B2
(45) Date of Patent: Apr. 10, 2007

(54) OPTICALLY SIMILAR REFERENCE SAMPLES

(75) Inventors: Howland D. T. Jones, Edgewood, NM (US); David J. Nunez, Albuquerque, NM (US); Stephen J. Vanslyke, Albuquerque, NM (US); Robert D. Johnson, Albuquerque, NM (US); Edward L. Hull, Albuquerque, NM (US)

(73) Assignee: InLight Solutions, Inc., Albuquerque, NM (US)

(*) Notice: Subject to any disclaimer, the term of this patent is extended or adjusted under 35 U.S.C. 154(b) by 552 days.

(21) Appl. No.: 10/281,576

(22) Filed: Oct. 28, 2002

(65) Prior Publication Data
US 2004/0082070 A1 Apr. 29, 2004

Related U.S. Application Data

(63) Continuation-in-part of application No. 09/832,608, filed on Apr. 11, 2001, now Pat. No. 6,983,176.

(51) Int. Cl.
*G01N 21/00* (2006.01)
*G01N 21/35* (2006.01)

(52) U.S. Cl. .................. 436/164; 436/8; 436/165; 436/166; 422/82.05; 422/82.09; 356/51; 356/300; 356/317; 600/310; 600/473; 600/476

(58) Field of Classification Search .............. 436/8, 436/19, 164–166; 252/408.1; 356/300, 356/317, 51; 422/82.05, 82.09; 600/476, 600/310, 473
See application file for complete search history.

(56) References Cited

U.S. PATENT DOCUMENTS

| | | | | |
|---|---|---|---|---|
| 4,774,957 A | * | 10/1988 | Nambu et al. | 600/414 |
| 4,843,866 A | * | 7/1989 | Madsen et al. | 73/1.86 |
| 5,053,341 A | * | 10/1991 | Companion | 436/8 |
| 5,166,517 A | | 11/1992 | Volgyesi | 250/252.1 |
| 5,278,627 A | | 1/1994 | Aoyagi et al. | 356/41 |
| 5,531,786 A | * | 7/1996 | Perry et al. | 623/8 |

(Continued)

FOREIGN PATENT DOCUMENTS

| | | | |
|---|---|---|---|
| EP | 368436 | * | 5/1990 |
| WO | WO 01/14496 A1 | | 8/2000 |
| WO | WO 01/36000 A1 | | 11/2000 |
| WO | WO 01/58344 A1 | | 1/2001 |

OTHER PUBLICATIONS

U.S. Appl. No. 09/415,594, filed Oct. 8, 1999, Rowe et al.

(Continued)

*Primary Examiner*—Maureen M. Wallenhorst
(74) *Attorney, Agent, or Firm*—V. Gerald Grafe

(57) ABSTRACT

Systems and methods for establishing and/or maintaining the accuracy of a multivariate calibration model designed for quantitative optical spectroscopic measurement of attributes or analytes in bodily tissues, bodily fluids or other biological samples, which are particularly useful when the spectral absorbance of the attribute or analyte is small relative to the background. The present invention provides an optically similar reference sample to reduce the effect of instrument or environment variation on the measurement capability of the model. The optically similar reference can be a gel composition having scattering particles suspended therein. The reference gel can be directly applied to a spectroscopic instrument sampler, or can be in a container specifically designed for optimal coupling to a spectroscopic instrument.

47 Claims, 18 Drawing Sheets

U.S. PATENT DOCUMENTS

| | | | |
|---|---|---|---|
| 5,625,137 A * | 4/1997 | Madsen et al. | 73/1.84 |
| 5,830,132 A | 11/1998 | Robinson | 600/310 |
| 6,045,502 A | 4/2000 | Eppstein et al. | 600/306 |
| 6,212,424 B1 | 4/2001 | Robinson | 600/475 |
| 6,224,969 B1 | 5/2001 | Steenbergen et al. | 428/313.3 |
| 6,226,541 B1 | 5/2001 | Eppstein et al. | 600/407 |
| 6,404,497 B1 * | 6/2002 | Backman et al. | 356/369 |
| 6,983,176 B2 * | 1/2006 | Gardner et al. | 600/310 |

OTHER PUBLICATIONS

*NATROSOL Hydroxyethylcellulose—A nonionic Water-Soluble Polymer*—Physical and Chemical Properties.

Douglas A. Skoog and James J. Leary, *Principles of Instrumental Analysis*—Fourth Edition Chapter 7, *An Introduction to Molecular Ultraviolet/Visible and Near-Infrared Absorption Spectroscopy*, pp. 123-149.

Allan S. Hoffman, *Hydrogels fro Biomedical Applications*, Advanced Drug Delivery Review 43 (2002) pp. 3-12.

Guillermo Marque, Lihong V. Wang, Changjie Wang and Zhibing Hu, *Development of Tissue-Simulating Optical Phantoms: Poly-N-Isopropylacrylamide Solution Entrapped Inside a Hydrogel*, Phys. Med. Biol. 44 (1999) pp. 309-318.

Michael Firbank, Motoki Oda and David T. Delpy, *An Improved Design for a Stable and Reproducible Phantom Material for Use in Near-Infrared Spectroscopy and Imaging*, Phys. Med. Biol. 40 (1995) pp. 955-961.

* cited by examiner

OPTICALLY SIMILAR REFERENCE SAMPLES

CROSS REFERENCES TO CO-PENDING APPLICATIONS

This application claims priority under 35 U.S.C § 120 as a continuation-in-part of U.S. patent application Ser. No. 09/832,608, entitled "Optically Similar Reference Samples and Related Methods for Multivariate Calibration Models Used in Optical Spectroscopy," filed Apr. 11, 2001, now U.S. Pat. No. 6,983,176, Jan. 3, 2006, incorporated herein by reference.

FIELD OF THE INVENTION

The present invention generally relates to calibration reference samples and techniques for multivariate calibration models used in optical spectroscopy. More specifically, the present invention relates to calibration reference samples and techniques for building and maintaining multivariate calibration models used in optical spectroscopy for the measurement of characteristics such as analyte concentration in tissue by utilizing a reference sample that is optically similar to the tissue.

BACKGROUND OF THE INVENTION

Optical spectroscopy can be used to determine characteristics and concentrations of constituents in samples. See, e g., Skoog, D. A. and J. J. Leary, Principles of Instrumental Analysis, Fort Worth: Saunders, 1992. In some applications, however, changing measurement conditions, such as instrument and environment changes, can lead to undesirable errors. Accordingly, there is a need for devices and methods that can reduce such errors, for example in the quantitative optical spectroscopic measurement of attributes or analytes in bodily tissue, blood or other biological samples. Such devices and methods can be especially useful when the spectral absorbance of the attribute or analyte is small relative to the total absorbance of the sample.

SUMMARY OF THE INVENTION

The present invention provides systems and methods for establishing and/or maintaining the prediction capability over time of a multivariate calibration model designed for quantitative optical spectroscopic measurement of attributes of or analytes in bodily tissues, bodily fluids or other biological samples, including plant samples, animal samples, food products, and derivatives thereof (e.g., human tissue, cheese, fruit, etc.). The present invention is particularly useful in spectroscopic measurement of attributes or analytes when the spectral absorbance of the attribute or analyte is small relative to the background, and stable calibration samples are not readily available. To accomplish this, the present invention uses an optically similar reference sample ("OSRS"). An OSRS can be used to capture variation present in the optical system so that measurement performance can be maintained. The ability to capture instrument and environmental variation can be enhanced by the use of an OSRS. An OSRS is similar to the test sample in terms of spectral radiance under the conditions of interest. An OSRS can be reproducible over time and designed such that its optical properties are sufficiently matched to the sample of interest that instrument and environmental variations are captured in a similar manner in both the sample of interest and the OSRS.

The turbid medium characteristics of biological tissue can complicate optical spectroscopic measurements. Turbid media generally do not permit any single ray of light to follow an undisturbed pathway through the medium. In effect, turbid media are non-deterministic. That is, a light ray that enters a turbid medium may undergo several scattering events before finally exiting the medium. When many light rays are directed into a turbid medium, each of the exiting rays collected at any given point will have traveled a different distance through the medium. As a result, a spectrum from a turbid medium source is determined not only by type and concentration of the molecular species in the medium, but also by the shape of the pathway distribution the light took to travel through the medium.

In human tissue, water is a significant constituent of the turbid medium. With respect to soft tissue such as the dermis, a reasonable water concentration is 75% by volume. Because light entering the tissue undergoes multiple scattering interactions, the light rays exiting the tissue will have traveled different pathlengths through the tissue and through the primary constituent water. The resulting spectrum is the summation of many different light rays that have traveled different pathlengths through water. Thus, a spectrum of tissue is composed of many different pathlengths of water. It has been found that an OSRS of the present invention that optically interacts with the optical measurement system in a manner that simulates tissue preferably produces an optical interaction that results in multiple different pathlengths of water.

As used herein, a "calibration model" is any set of coefficients or associated algorithms that are used in the generation of a measurement result. A "test sample" is a sample in which the measurement of the attribute is being made. A "reference spectrum" is any optical measurement information obtained in conjunction with an OSRS, and can be full spectrum in nature or any part of the measured response, to include individual wavelengths, and includes information derived from the reference spectrum. A "sample of interest" refers to an analyte-containing or attribute-containing spectral sample, such as human bodily tissue (e.g. skin), human bodily fluid (e.g., blood) or other biological sample, whose composition or physical properties are being determined or measured. A "spectroscopic determination" or "spectroscopic measurement" refers to a determination of a property or composition of a test sample from characteristics of the sample's interaction with light, including interactions with light at one or more identified wavelengths.

An OSRS according to the present invention can be quantitatively described in terms of spectral radiance (W/m$^2$Sr=watts per square meter per steradian). An OSRS can exhibit substantially the same mapping of input spectral radiance (W/m$^2$Sr) to spectral radiant excitance (W/m$^2$Sr) as does the sample of interest. This definition of spectral similarity can be broken down into several sub-categories, all of which are implicitly incorporated into spectral radiance: spectral absorption features, overall light intensity received by the optical detector elements, angular distribution of light emitted by the sample, and spatial distribution of light emitted by the sample. The degree of spectral similarity required for calibration maintenance is dependent on the types and magnitudes of instrumental and environmental variations for which the model must compensate as well as the sensitivity of the model to those variations and the level of the signal due to the analyte. An OSRS according to the present invention can provide spectral similarity, spatial similarity, angular similarity, and combinations thereof.

An OSRS according to the present invention is useful for establishing and maintaining a quantitative calibration model for measuring an analyte or attribute whose spectral signature is much smaller than that of the surrounding matrix in a sample of interest. The use of an OSRS for calibration maintenance is applicable to several different methods of optical spectroscopy, including reflectance and transmission spectroscopy, for both in vivo and in vitro measurements of a variety of types of samples of interest.

The present invention is suitable for, but not limited to, the following applications. The present invention can be useful in measurements of blood constituents including glucose, alcohol, BUN (blood urea nitrogen), bilirubin, hemoglobin, creatinine cholesterol, and electrolytes as disclosed in U.S. Pat. No. 5,830,132 to Robinson, entitled Robust Accurate Non-Invasive Analyte Monitor, incorporated herein by reference. The present invention can also be useful in spectroscopic monitoring of kidney dialysis as disclosed in U.S. Pat. No. 6,212,424, issued on Apr. 3, 2001, entitled "Apparatus and Method for Determination of the Adequacy of Dialysis by Non-Invasive Near-Infrared Spectroscopy", incorporated herein by reference. The present invention can also be useful in spectroscopic identification of people as disclosed in U.S. Pat. No. 6,628, 809, issued on Sep. 30, 2003, entitled "Apparatus and Method for Identification of Individuals by Near-Infrared Spectrum", incorporated herein by reference. The present invention can be useful in maintenance of classification calibration models such as those used for distinguishing between malignant and benign tumors. Those skilled in the art will recognize that the present invention has other applications not specifically mentioned herein.

An OSRS according to the present invention can include one or more components or constituents that are optically measured in a manner that closely mimics the optical measurement of the test sample of interest. The construction and composition of an OSRS can depend on a number of factors, including: the wavelength region of light used, the optical properties of the sample of interest, and the characteristics of the spectroscopic instrumentation. To achieve spectral similarity, an OSRS can contain some of the same components or constituents as the sample of interest (e.g., water, collagen, protein, lipids). The components or constituents can be natural animal or plant products or can also be synthesized. Specifically, organic polymers can be used in the creation of an OSRS. An OSRS can also include a concentration of the analyte of interest or of tissue with a property of interest. Spectral similarity can also be achieved using alternative components (e.g., optical filter coatings, optical scattering media, or diffuse reflectance material) with spectral characteristics similar to the components and constituents contained in the sample of interest.

The present invention provides a number of different OSRS embodiments. In each, an OSRS creates a spectral absorbance similar to that of the test sample. In other words, the OSRS absorbs the same or similar intensity of light at wavelengths in the range of wavelengths measured. Alternatively, the OSRS can absorb a similar relative intensity of light at each selected wavelength over the range of wavelengths measured. The similar relative absorbance will result in a similar spectral shape, while the average absorbance value of the resulting spectra may be different. With this in mind, those skilled in the art will recognize other types of reference samples without departing from the scope or spirit of the present invention. Thus, the following examples are provided for purposes of illustration, not limitation.

The method of the present invention provides for use of an OSRS in a spectroscopic determination. An optical spectroscopy system used in the spectroscopic determination can include an optical spectrometer having an illumination source (e.g., a source of near-infrared radiation), a collection system, and an OSRS optically coupled (e.g., disposed adjacent) to the illumination source and collection system. A background sample using an OSRS can be measured using the exact same system and methodology as that used for the test sample of interest. Alternatively, the background sample can have a separate interface with the instrument. In some embodiments, the OSRS is composed of multiple components that are simultaneously measured at different locations in the optical path of the spectroscopic instrument. In some embodiments, the OSRS can be designed for either manual or automatic placement into the correct location for optical sampling. Automatic placement allows for automated obtainment of the reference spectrum and can enable calibration maintenance without the direct intervention of an operator.

The present invention provides a method of establishing an accurate calibration model and/or maintaining the accuracy of an optical measurement system by using an OSRS as described above. In one embodiment, a reference spectrum is obtained from the OSRS using an optical system and the calibration model is created or modified based on use of the calibration data and the reference spectrum. One such method is to use a linear combination of the calibration data and reference spectra. The combinations of calibration data and reference data can be done in a structured or random way. It has been found that random associations work effectively and are easily implemented. The process of creating these composite data is referred to as robustification. The resulting calibration spectra contain the reference spectra from the OSRS combined with calibration data. The resulting data contains spectroscopic variation associated with the instrument and environmental state of the instrument. The composite calibration data can be processed to develop a calibration model. Utilizing the newly created or modified calibration model, an analyte or attribute of the test sample is determined based on the test spectrum. In another embodiment, the determination of the analyte or attribute of the test sample can be based on a test spectrum that has been modified by the reference spectrum. The modified test spectrum is used as an input to create the model or as input to an existing model to predict the analyte or attribute. The modification by, or use of, the reference spectrum helps compensate for, or account for, instrument or environmental changes. In another embodiment, multiple OSRSes are used to create multiple reference spectra.

The reference spectrum can be obtained just prior to obtaining the test spectrum. To increase accuracy, multiple reference spectra can be obtained near in time to obtaining the test spectrum. The multiple reference spectra can be obtained over a period of time and averaged or combined with a time-weighted scheme just prior to obtaining the test spectrum.

DETAILED DESCRIPTION OF THE INVENTION

Figure 1:
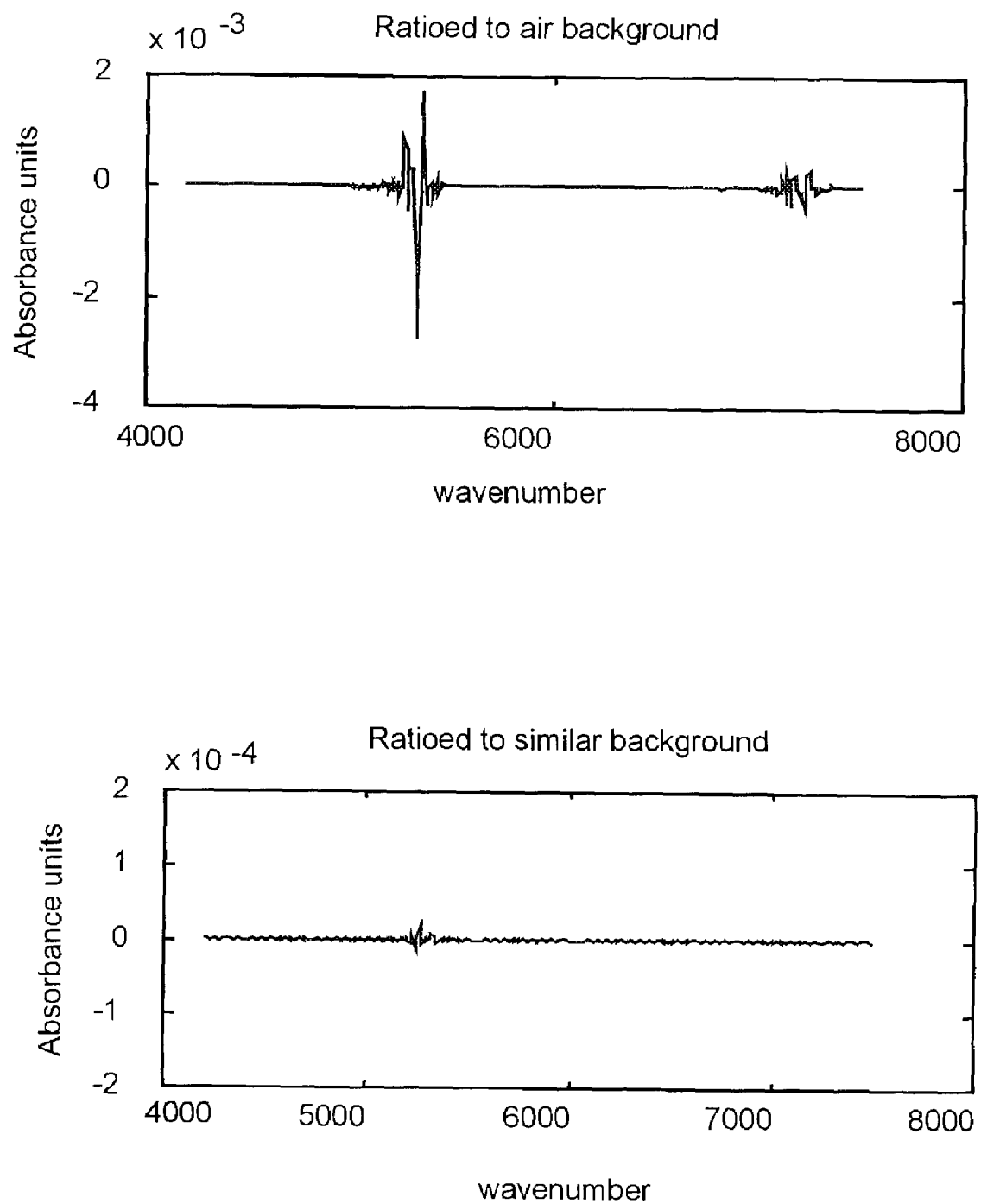
FIG. 1 is a graphical representation of spectral residuals comparing a conventional air background to an OSRS in accordance with the present invention.

The drawings, which are not necessarily to scale, depict illustrative embodiments and are not intended to limit the scope of the invention.

For the purposes of the application, the term "about" applies to all numeric values, whether or not explicitly indicated. The term "about" generally refers to a range of numbers that one of skill in the art would consider equivalent to the recited value (i.e., having the same function or result). In some instances, the term "about" can include numbers that are rounded to the nearest significant figure.

Benefits of an OSRS

To better appreciate the operation of and the benefits afforded by the present invention, it is useful to analytically review the problem at hand. The present invention addresses the difficulty in maintaining a multi-wavelength calibration model for measuring the concentration of analytes or tissue properties whose spectral absorption is much smaller than that of the gross sample spectrum. The cause of the failure of a spectrally dissimilar reference sample to maintain calibration under these conditions can be described analytically as shown below.

Photometric inaccuracies can be present even in an ideal instrument of finite resolution where all sources of non-linearity (detector response, stray light, etc.) have been removed. See, e g., R. J. Anderson and P. R. Griffiths, *Analytical Chemistry*, Vol. 47, No. 14, December 1975; R. J. Anderson and P. R. Griffiths, *Analytical Chemistry*, Vol. 50, No. 13, November 1978. This inherent inaccuracy is caused by the finite resolution of the instrument (grating spectrometer or FT interferometer) because a spectrum produced by an instrument with finite resolution will be the true sample spectrum convolved with the instrument line shape (ILS) (for a grating spectrometer, the ILS is a function of the entrance and exit slit widths; for an FT interferometer, the ILS is a function of the instrument self-apodization and the apodization function used in performing the Fourier transform). One can think of the convolution process as a distortion of the true spectrum at a particular wavenumber that is dependent on all other spectral intensities within the spectral bandpass of the instrument. Mathematically this can be written as Equation (1).

$$T^a(\bar{v}_l) = \int_0^\infty \sigma(\bar{v} - \bar{v}_l) e^{-K(\bar{v})l} d\bar{v} \qquad \text{Eq. (1)}$$

In Equation 1, $T^a(\bar{v}_l)$ is the measured (or apparent) transmission at a particular optical frequency, $\bar{v}_l$, $\sigma$ defines the ILS (or apodization), $K(\bar{v}_l)$ is the absorption coefficient of the species being observed and l is the pathlength through the sample. A conclusion drawn from the Griffiths paper is that this apodization induced distortion causes significant deviations from Beer's law when the true absorbance of a peak exceeds 0.7 AU.

Deviations from Beer's law are also a function of the instrument resolution relative to the narrowness of the spectral line being measured. A quantity called the resolution parameter, $\rho$, is defined as the ratio of the instrument resolution, R, to the full-width-half-height (FWHH) of the spectral band of interest as set forth by Equation (2):

$$\rho = R/FWHH \qquad \text{Eq. (2)}$$

The effect of $\rho$ on photometric accuracy can be understood in the limit by examining Equation (1). If the ILS is thought of as a Dirac-delta or impulse function (i.e., perfect instrument resolution), then the ILS convolution in Equation (1) yields the absorbance term independent of ILS, in other words the true absorbance spectrum is measured if the instrument operates with infinite resolution. On the other hand, if the absorbance term is thought of as a delta function, we are left with only the ILS centered at the discrete wavelength where the absorption line occurs. Accordingly, photometric inaccuracy due to apodization is a function of both p and the spectral absorbance of the sample as set forth in Equation (3), where $A^T(\bar{v})$ is the true absorbance of all absorbers in the sample.

$$\text{Error} = f\{\rho, A^T(\bar{v})\} \qquad \text{Eq. (3)}$$

When there are different absorbers in the sample and background (for example, liquid water, glucose and water vapor in the sample and only water vapor in the background), the background will not capture some system perturbations in the same way that the sample will record the same perturbations. The strategy for using a background in spectroscopy is to capture and correct for instrumental or environmental variations so that the true absorbers in the sample can be identified. If the coefficients of absorption are included for all absorbers in the system, Equation (1) can be rewritten to represent the measured transmission of any sample in any environment. As an example, for the particular case of glucose in water in the presence of water vapor, Equation (1) becomes Equation (4).

$$T_s^A(\bar{v}_i) = \int_0^\infty \sigma(\bar{v}-\bar{v}_i) e^{-K_l(\bar{v})l_l} e^{-K_g(\bar{v})l_g} e^{-K_w(\bar{v})l_w} e^{-K_v(\bar{v})l_v} d\bar{v} \quad \text{Eq. (4)}$$

In Equation 4, the subscript "l" represents instrument, "g" represents glucose, "w" represents liquid water and "v" represents water vapor present in the measuring environment. A typical background sample spectrum containing no glucose or water can be written as Equation (5).

$$T_b^A(\bar{v}_i) = \int_0^\infty \sigma(\bar{v}-\bar{v}_i) e^{-K_l(\bar{v})l_l} e^{-K_v(\bar{v})l_v} d\bar{v} \quad \text{Eq. (5)}$$

In Equation 5, the background spectrum measures the instrument absorbance and the water vapor absorbance. The background corrected sample spectrum can be written as Equation (6).

$$\frac{T_s^A(\bar{v}_i)}{T_b^A(\bar{v}_i)} = \frac{\int_0^\infty \sigma(\bar{v}-\bar{v}_i) e^{-K_l(\bar{v})l_l} e^{-K_g(\bar{v})l_g} e^{-K_w(\bar{v})l_w} e^{-K_v(\bar{v})l_v} d\bar{v}}{\int_0^\infty \sigma(\bar{v}-\bar{v}_i) e^{-K_l(\bar{v})l_l} e^{-K_v(\bar{v})l_v} d\bar{v}} \quad \text{Eq. (6)}$$

As shown in Equation (1) the spectral intensity at each optical frequency depends on the spectral intensity of the adjacent frequencies measured by the instrument, the absorption terms for the instrument $e^{-K_l(\bar{v})l_l}$ and the water vapor $e^{-K_v(\bar{v})l_v}$ do not cancel in Equation (6), resulting in a background corrected spectrum that is not equal to the true absorbance spectrum of the measured analytes. These terms only cancel if all other absorption terms that are not common to both sample and background are negligible or do not vary with optical frequency. Equation (6) can be expanded further to encompass any instrumental or environmental perturbation from the calibration state as set forth by Equation (7), where the subscript $\Delta$ represents the absorption due to the perturbation.

$$\frac{T_{s+\Delta}^A(\bar{v}_i)}{T_{b+\Delta}^A(\bar{v}_i)} = \frac{\int_0^\infty \sigma(\bar{v}-\bar{v}_i) e^{-K_l(\bar{v})l_l} e^{-K_g(\bar{v})l_g} e^{-K_w(\bar{v})l_w} e^{-K_v(\bar{v})l_v} e^{-K_\Delta(\bar{v})l_\Delta} d\bar{v}}{\int_0^\infty \sigma(\bar{v}-\bar{v}_i) e^{-K_l(\bar{v})l_l} e^{-K_v(\bar{v})l_v} e^{-K_\Delta(\bar{v})l_\Delta} d\bar{v}} \quad \text{Eq. (7)}$$

Maintenance of calibration can be achieved using any reference sample if the ratio in Equation (7) were equal to the ratio in Equation (6). However, as long as the unknown sample and reference sample have different spectral characteristics, Equation (7) will not identically equal Equation (6). The two equations become more similar as the reference sample begins to absorb more like the prediction sample.

A similar background is useful when the system perturbation is not well modeled and the perturbation is not negligible in magnitude compared to the absorbers in the prediction sample, or when the spectral resolution (full width at half height) of the perturbation is much less than the instrument resolution. Another way to write this requirement is in terms of the final regression coefficients from a multivariate calibration model acting on the spectrum of the unknown sample. This can be written as Equation (8).

$$\vec{F} \cdot (\vec{S}_o + \vec{S}_{NL} + \vec{\epsilon}) \Rightarrow \vec{F} \cdot \vec{S}_{NL} << \vec{F} \cdot \vec{\epsilon} \quad \text{Eq. (8)}$$

In Equation 8, $\vec{F}$ represents a vector of final regression coefficients, $\vec{S}_o$ represents the true spectrum, $\vec{S}_{NL}$ represents the distorted, or non-linear, part of the measured spectrum due to the finite resolution of the instrument and $\vec{\epsilon}$ represents the spectral error due to sources of random error. In other words, the product of the final regression coefficients and the non-linear portion of the measured spectrum caused by a system perturbation should be much less than the product of the final regression coefficients and the random error present in the measured spectrum so that the error term due to the distorted part of the spectrum is small and prediction performance is maintained.

Several types of instrumental and environmental variation can affect the prediction capability of a calibration model. It is possible to reduce the effect of instrumental and environmental variation by incorporating the variations into the calibration model. It can be difficult, however, to span the entire possible range of instrument states during the calibration period. System perturbations can result in the instrument being operated outside the space of the calibration model. Measurements made while the instrument is in an inadequately modeled state can exhibit errors that render the measurement useless. In the case of medical measurements, these types of errors can result in erroneous medical information being used for the treatment of patients. These errors are unacceptable in some applications.

Some examples of problematic instrument and environmental variation include, but are not limited to: changes in the levels of environmental interferants such as water vapor or $CO_2$ gas, changes in the alignment of the instrument's optical components, fluctuations in the output power of the instrument's illumination system, and changes in the spatial and angular distribution of the light output by the instrument's illumination system. Both simulated and empirical results show that an OSRS provides improved capability to correct for these types of variations.

An OSRS with spectral absorption features matched to the sample of interest can correct for instrument and environmental variation. It has already been shown mathematically that finite instrument resolution causes the effect of different instrument states to depend on the spectral absorption characteristics of the sample (Equation (7)). Another way of stating this problem is that the optical effects of instrument and environmental variation should be identical in both the background sample and the sample of interest. Taking the derivative of Equation (4) with respect to water vapor absorption yields Equation (9), which shows that the spectrum of water vapor is modified by the spectral shape of all compounds in the sample. This relationship holds true for any system perturbation that causes a change in the optical appearance of a sample's spectrum.

$$\frac{dT_s^A(\bar{v}_i)}{dK_v(\bar{v})} = \int_0^\infty -l_v \sigma(\bar{v}-\bar{v}_i) e^{-K_l(\bar{v})l_l} e^{-K_g(\bar{v})l_g} e^{-K_w(\bar{v})l_w} e^{-K_v(\bar{v})l_v} d\bar{v} \quad \text{Eq. (9)}$$

A properly-designed OSRS can also mitigate other types of errors. For example, when measurements of an optically scattering medium such as human tissue are made, the detected photons have typically traversed a variety of pathlengths through the sample of interest. In addition to matching the overall measured absorbance of the sample of interest, it can be desirable that the OSRS return photons having the same distribution of pathlengths as those collected from the sample of interest. The distribution of photon pathlengths is governed in part by the sample's scattering coefficient ($\mu_s$), which is defined as the inverse of the distance that a photon will travel, on average, between scattering events. It can also be advantageous to match the distribution of scattering angles of the photons returned from the OSRS to corresponding distribution of the sample of interest. The distribution of scattering angles is governed in part by the sample's scattering phase function, $p(\theta)$, which is defined as the probability that a photon will, upon scattering, deflect through an angle $\theta$. The first moment of the scattering phase function, the scattering anisotropy, is defined as the average cosine of the scattering angle, and can be a desirable matching characteristic for an OSRS. Accomplishing these types of spectroscopic similarity can, for example, mitigate errors introduced by drift in the angular distribution of light emerging from the illumination system.

Sample Results

Simulated results discussed below demonstrate the advantage of using an OSRS for correcting for even simple system perturbations. Simulated results are presented for the effects of water vapor level variation on the in vitro measurement of glucose in reflectance using scattering media. Actual spectra from 98 glucose solution samples were collected using an FTIR spectrometer operated at 16 cm$^{-1}$ resolution. The samples contained variable levels of scattering media to simulate optical pathlength distributions similar to those seen in living tissue. For comparison purposes, spectra from two different types of background samples were also collected: an OSRS with matched optical properties, and an air background (i.e. an integrating sphere placed over the reflectance sampler). High-resolution water vapor spectra (obtained at 1 cm$^{-1}$) were then artificially added to the solution and background spectra in order to simulate varying water vapor levels. Simulations on the resulting spectra modeled the effects of finite instrument resolution on the added interferants. The sample spectra were then adjusted with the background sample spectra to remove the effects of the varying water vapor levels.

FIG. 1 shows the residual spectral effects after this background correction was performed. The two plots in FIG. 1 show the remaining spectral differences when the adjusted spectra with added water vapor are subtracted from the original adjusted spectra without added water vapor. As can be seen in the figure, the OSRS reduces the effects of the water vapor interferant by a significant amount. A calibration developed at a constant water vapor was used to make determinations of a sample spectra. As stated above, the sample spectra were ratioed against an OSRS with matched optical properties and an air background. The prediction errors for the sample data with the air background ratio were inflated over the sample spectra with OSRS by approximately 40 mg/dL.

Many types of instrument variation involve interactions with the sampling geometry of the sample. These types of instrument variation include changes in alignment of optical components and changes in angular and spatial distribution of the output light from the instrument's illumination system. These types of variations can be caused by a number of physical mechanisms, including aging of optical mounts, thermally induced mechanical deformations of optical mounts, aging of light sources, and variations in routinely replaced components such as light bulbs. An OSRS can exhibit the same mapping of angular and spatial distribution of light as the sample of interest. The OSRS thus interacts with the sampling optics of the instrument in a manner that mimics the interaction of the sampling optics with the sample of interest.

An additional constraint that can be required for calibration maintenance is that the overall intensity of light seen at the optical detector elements be closely matched for both the background sample and the sample of interest. This constraint can decrease errors due to non-linearities in the instrument's characteristics (e.g., optical or electrical measurement non-linearities).

Figure 2:
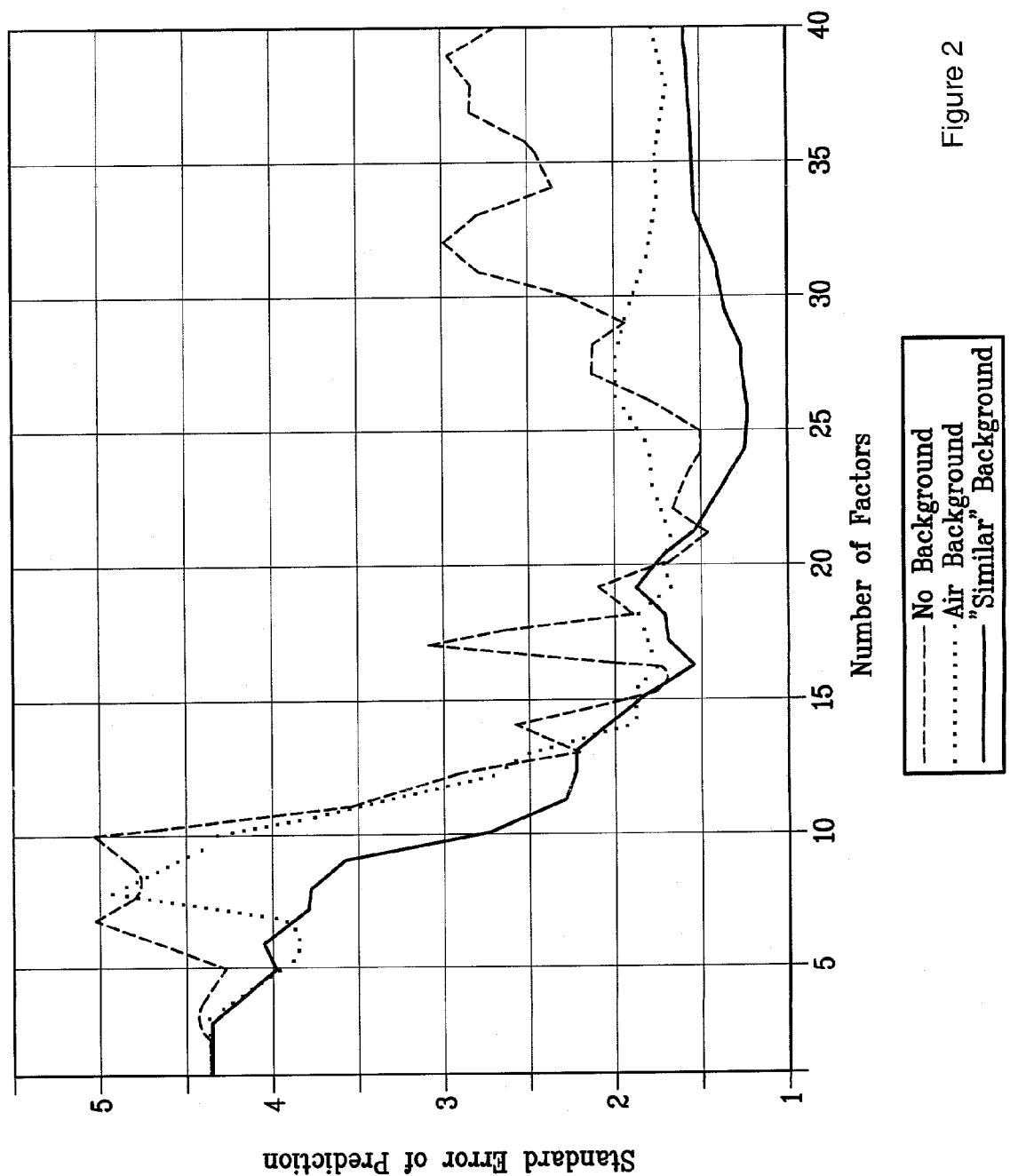
FIG. 2 is a graph representing standard error of prediction comparing no background, a conventional air background, and an OSRS in accordance with the present invention in the presence of instrument and environmental variation.
Figure 3:
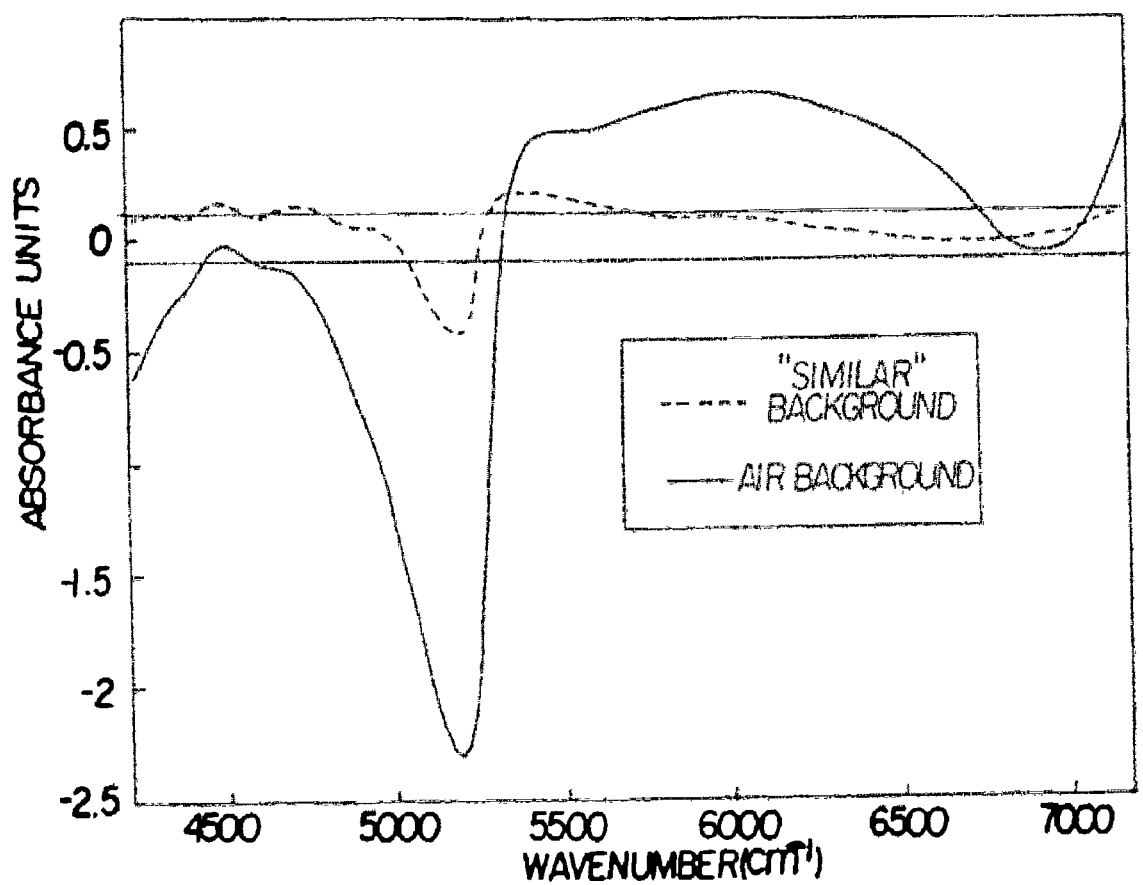
FIG. 3 is a graph of the spectral differences between the mean human tissue spectrum and two different backgrounds, namely a conventional air background and an OSRS in accordance with the present invention.

Experiments demonstrate the performance benefits of an OSRS in an actual, in vivo study measuring blood glucose concentrations non-invasively. The study included several of the types of instrument and environmental variation previously discussed herein. Specifically, ambient relative humidity, ambient temperature, and illumination power all varied during the measurement phase of the study. The study was limited to five subjects over a period of two days. Measurement errors were determined by comparing non-invasive results to standard capillary blood glucose reference measurements. FIG. 2 demonstrates the superior ability of the OSRS to maintain the prediction performance of the calibration in the presence of instrument and environmental variation by generating a lower standard error of prediction (SEP) and by generating the smoothest decreasing SEP curve. FIG. 3 shows the spectral differences between the mean human tissue spectrum and the two different background sample types being tested in the study.

Figure 4:
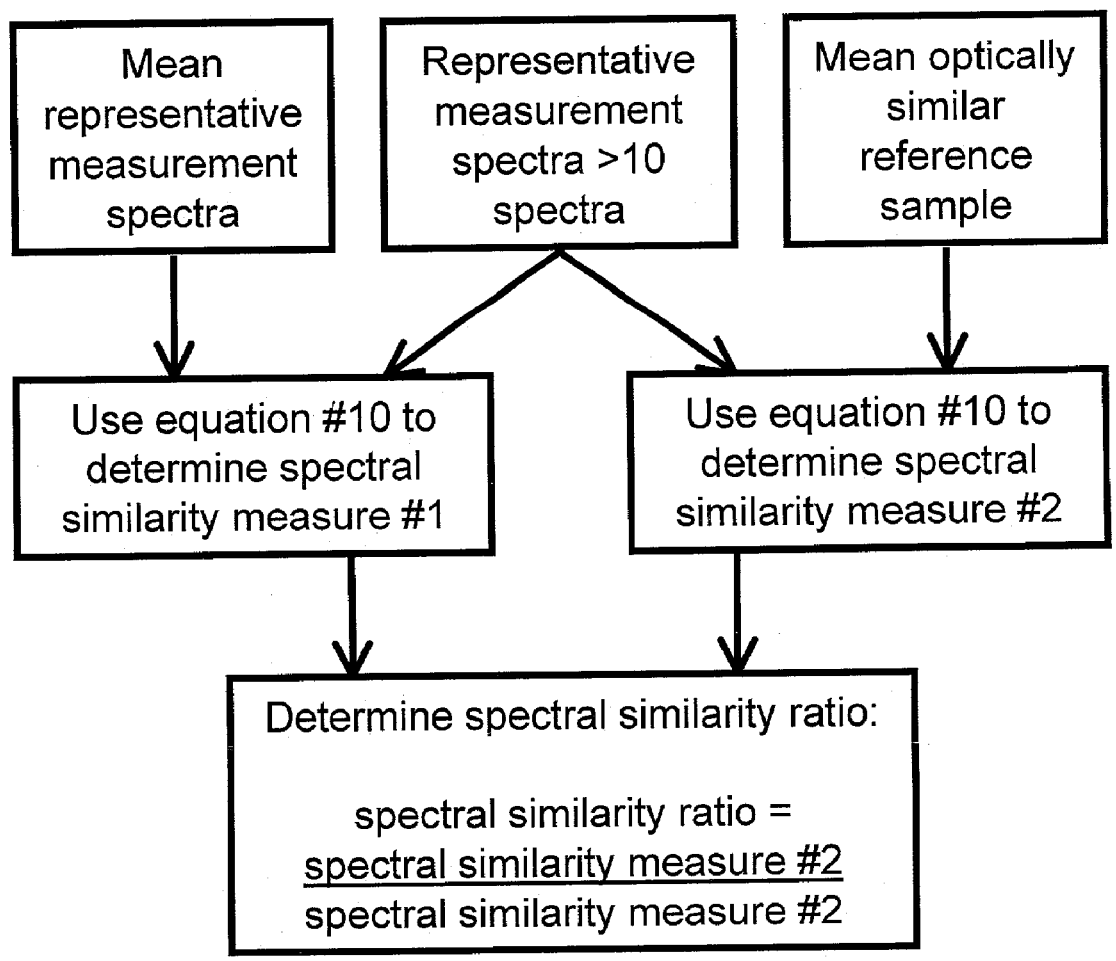
FIG. 4 is a flowchart illustrating the steps used in quantifying spectral similarity.

FIG. 4 is a flowchart for determining spectral similarity. FIGS. 5–10 show various embodiments of OSRSes of the present invention, and show various graphs demonstrating the improved performance with the use of an OSRS. Each OSRS discussed with reference to FIGS. 5–10 provides a background that has a spectrum that is similar to the test sample. In other words, the OSRS absorbs the same or similar intensity of light at each wavelength over the range of selected relevant wavelengths measured as does the sample of interest.

The spectral similarity of an OSRS to the test sample of interest can be quantified with respect to spectral absorbance, mapping of input to output light spatial distribution, and mapping of input to output light angular distribution.

Two metrics can be used to calculate the similarity of a particular background sample to the sample of interest with respect to spectral absorbance. The first involves comparing the OSRS to the test samples, typically tissue spectra, where all of the background and tissue spectra were collected near in time, as set forth in Equation 10.

$$\text{Spectral Similarity} = \frac{\sum_{i=1}^{I}\left(\sum_{j=1}^{J}(X_{ij}-z_i)^2\right)}{I} \qquad \text{Eq. (10)}$$

In Equation 10, X is a set of tissue pseudo-absorbance spectra and z is any mean background pseudo-absorbance spectrum for the time in question (the pseudo-absorbance spectrum is defined in Equation 11, where I is a single beam intensity spectrum). l refers to the total number of data points collected in the wavelength region of interest (or the total number of discrete wavelengths chosen for analysis), and J refers to the total number of tissue spectra collected in this period of time. The average value of the spectrum can be subtracted from all wavelengths before calculating the metrics to reduce the influence of a uniform, DC energy offset or baseline shift.

$$\text{Pseudo-absorbance} = -\log_{10}(I) \quad \text{Eq. (11)}$$

Quantifying the degree of spectral similarity can be done through a straightforward process involving a comparison between the spectra of the sample of interest and the OSRS. The flowchart of FIG. 4 summarizes this process. The process involves the following steps:

Step 1: Define or establish the representative measurement sample. A representative measurement sample is a sample that is representative of samples on which the optical measurement system will be making subsequent measurements. If the application is a single patient with diabetes, for example, then a sample at the sampling location on that patient can be a representative measurement sample. If the application group is a heterogeneous group of subjects, as another example, then samples from an appropriate group of subjects on which the monitor would be subsequently used can be the representative measurement samples. If the measurement group were other sub-populations of subjects, then the representative measurement samples would be obtained from the sub-population. For example, in patients with renal disease, patients with renal disease can be the representative measurement population.

Step 2: Obtain spectral measurements from the representative measurement samples. Multiple measurements with reinsertion of the tissue into the sampling device can be useful. In the case of a single subject application, ten or more spectral measurements can be made. In the case of a heterogeneous patient population, the representative measurement samples can be a reflection of the subjects that will subsequently use the monitor. In the example below, 30 subjects of varying ages, gender, ethnicity and body mass index were used. The spectral measurements should be made in a manner consistent with use of the monitoring device. These spectra are hereafter referred to as the representative measurement spectra.

Step 3: Calculate a mean pseudo-absorbance spectrum from the spectra obtained from the representative measurement samples. The resulting spectrum is hereafter referred to as the mean representative measurement spectrum.

Step 4: Obtain spectral measurements from the OSRS. Multiple insertions and measurements of the OSRS can be useful; for example, 10 or more measurements can be made. These spectra are hereafter referred to as the OSRS spectra.

Step 5: Calculate a mean pseudo-absorbance spectrum from the OSRS spectra. The resulting spectrum is hereafter referred to as the mean optically similar reference spectrum.

Step 6: Use the representative measurement spectra and the mean representative measurement spectrum with Equation #10 to calculate a spectral similarity value. The resulting value will hereafter be referred to as the spectral similarity measure #1.

Step 7: Use the representative measurement spectra and the mean optically similar reference spectrum with Equation (10) to calculate a spectral similarity value. The resulting value will hereafter be referred to as the spectral similarity measure #2.

Step 8: Ratio the two spectral similarity values to obtain a spectral similarity ration, dividing spectral similarity measure #2 by spectral similarity measure #1.

Equation (10) is a mean sum of squares metric, and it can be calculated for different wavelength regions. It can be calculated for a continuous spectral region, for discrete wavelengths, for combinations of two or more discrete wavelengths (which may or may not have been found using a wavelength or variable selection algorithm), or for selected regions of a spectrum.

Table 1 below shows the values that were calculated for Equation (10) for a representative group of subjects for three levels of similarity. The spectral regions and discrete wavelengths for which these values were calculated are also indicated in the table. The discrete variables used in this case are glucose-important wavelengths (listed by wavenumber in $cm^{-1}$) and are specified in Table 2. The more similar the background is to the tissue spectra, the smaller the Spectral Similarity value becomes. Table 3 shows the same spectral similarity metrics when the representative sample is a single subject.

TABLE 1

| | Spectral Similarity Ratio | | |
|---|---|---|---|
| Example Background Sample | Full Spectrum ($4,200\ cm^{-1}$–$7,200\ cm^{-1}$) | Discrete Variables | Absorbance Troughs ($4,440\ cm^{-1}$–$4,800\ cm^{-1}$ & $5,400\ m^{-1}$–$6,400\ cm^{-1}$) |
| Scattering Solutions | 30 | 30 | 30 |
| Multipath Transmission Cell | 10 | 10 | 10 |
| Mean Subject Spectrum | 1 | 1 | 1 |

TABLE 2

Glucose-important variables used in spectral similarity calculations

| | | | | | | |
|---|---|---|---|---|---|---|
| 4196 | 4451 | 4883 | 5369 | 5731 | 6163 | 6696 |
| 4227 | 4459 | 4922 | 5392 | 5755 | 6187 | 6935 |
| 4273 | 4497 | 5014 | 5454 | 5785 | 6287 | 6973 |
| 4281 | 4528 | 5091 | 5469 | 5809 | 6318 | 7004 |
| 4304 | 4559 | 5176 | 5477 | 5839 | 6349 | 7043 |
| 4320 | 4613 | 5230 | 5515 | 5893 | 6449 | 7066 |
| 4335 | 4690 | 5269 | 5585 | 5924 | 6472 | 7205 |
| 4366 | 4775 | 5299 | 5623 | 5947 | 6557 | |
| 4389 | 4829 | 5315 | 5662 | 6001 | 6595 | |
| 4436 | 4860 | 5338 | 5701 | 6094 | 6673 | |

TABLE 3

| | Spectral Similarity Ratio | | |
|---|---|---|---|
| Example Background Sample | Full Spectrum ($4,200\ cm^{-1}$–$7,200\ cm^{-1}$) | Discrete Variables | Absorbance Troughs ($4,440\ cm^{-1}$–$4,800\ cm^{-1}$ & $5,400\ cm^{-1}$–$6,400\ cm^{-1}$) |
| Scattering Solutions | 1500 | 1500 | 7500 |
| Multipath Transmission Cell | 1000 | 1000 | 2500 |
| Mean Subject Spectrum | 1 | 1 | 1 |

If an analyte or specific characteristic is to be determined, it can be helpful if the background matches the regions or discrete wavelengths of the spectrum that are important in the determination. In other words, if spectral region A is important in determining the analyte or characterstic, then the background should match the tissue especially well in region A. On the other hand, if region A is not important in determining a different analyte, then the spectral match can be less important for that region. When an analyte or other characteristic is to be determined, therefore, another metric can be defined that is specific to the analyte in question, as shown in Equation (12), where b is the regression vector for the analyte being determined, normalized to length one, and the other symbols have the same meanings as in Equations (10) and (11).

$$\text{Regression weighted Similarity} = \frac{\sum_{i=1}^{I}\left(\sum_{j=1}^{J}(b_i * X_{ij} - b_i * z_i)^2\right)}{I} \quad \text{Eq. (12)}$$

This regression vector can be calculated via any linear or non-linear regression method, where partial least squares regression is an example of such a method. It can be thought of as the analyte's calibration model, and it weights the absorbances at different wavelengths based on their importance in predicting the analyte or characteristic of interest.

The process for quantifying the degree of spectral match is the same except that Equation (12) is used instead of Equation (10). The 8-step process is the same with a single substitution of the equations. The resulting ratio will hereafter be referred to as the regression weighted spectral similarity ratio.

Table 4 shows results from Equation (12), calculated for a representative group of subjects when the analyte of interest was glucose. These values can also be calculated for any component in the sample that is to be determined. The ideal background has a much smaller Spectral Similarity value than the acceptable background, since it is more similar to tissue spectra collected during the same period of time. The more similar the background is, the smaller the Spectral Similarity value will be for Equation (10) or Equation (12) or both, for any spectral region or any combination of regions or any discrete wavelength or combination of discrete wavelengths. Table 5 shows the same spectral similarity metrics when the representative sample is an individual subject. In an analysis where no specific characteristic (e.g., concentration) of the sample is being measured, then Equation (10) is sufficient. When a specific analyte or characteristic is to be determined, however, both Equations (10) and (12) may be evaluated.

As an example, the OSRS can be considered acceptable if the spectral similarity ratio for the OSRS is less than 30. The OSRS can be considered preferred if the spectral similarity ratio is less than 10. The OSRS can be considered ideal if the spectral similarity ratio is close to 1. The metrics should be calculated for the analyte being determined and for the wavelengths/wavelength regions being used to ensure the validity of the similarity determination.

TABLE 4

| Level of Similarity | Example Background Sample | Regression Weighted Spectral Similarity Ratio | | |
|---|---|---|---|---|
| | | Full Spectrum (4,200 cm$^{-1}$– 7,200 cm$^{-1}$) | Discrete Variables | Absorbance Troughs (4,440 cm$^{-1}$– 4,800 cm$^{-1}$ & 5,400 cm$^{-1}$– 6,400 cm$^{-1}$) |
| Acceptable | Scattering Solutions | 30 | 30 | 30 |
| Preferred | Transmission Cell | 10 | 10 | 10 |
| Ideal | Mean Subject Spectrum | 1 | 1 | 1 |

TABLE 5

| Level of Similarity | Example Background Sample | Regression Weighted Spectral Similarity Ratio | | |
|---|---|---|---|---|
| | | Full Spectrum (4,200 cm$^{-1}$– 7,200 cm$^{-1}$) | Discrete Variables | Absorbance Troughs (4,440 cm$^{-1}$– 4,800 cm$^{-1}$ & 5,400 cm$^{-1}$– 6,400 cm$^{-1}$) |
| Acceptable | Scattering Solutions | 4500 | 3000 | 9000 |
| Preferred | Transmission Cell | 1500 | 2500 | 3000 |
| Ideal | Mean Subject Spectrum | 1 | 1 | 1 |

The similarity of the mapping function of light spatial distribution and light angular distribution can also be quantified for OSRSes. One suitable method for quantifying the similarity of these properties is to examine the image of the output light beam produced after the light has passed through the sampling optics and the sample of interest. For purposes of this discussion, the light beam is assumed to be circular in cross-section, but the similarity metrics can be extended to any geometry of beam (e.g., the output of a square cross-section light guide). As a convention, the boundary of the light beam passing through the sample is defined as the points at which the light intensity falls to $1/e^2$ times the peak light intensity.

The image of the output beam can be measured using any standard intensity mapping scheme (e.g. scanning a single pixel detector or using a CCD camera), and by using a goniometer. This allows both the spatial and angular distributions of the light beam to be determined. Measurements should be made for both the sample of interest and for the OSRS being quantified. For some applications, the image can be divided into approximately one hundred equally sized "bins" (or squares), with ten bins across the diameter of the image, to standardize the calculation. This can be accomplished by measuring the beam in a ten by ten grid, or by sampling at a finer spacing and then averaging the data. The spatial and angular distributions for the sample of interest are then subtracted from the corresponding distributions of the background sample. The resulting images represent the similarity level for the background and the sample of interest. All of the data points in the image can be put into a vector for easier calculation, and the vector normalized so that its length equals 1. This can be achieved by dividing each data point in the image by the 2-norm ($\|x\|_2$), which is equivalent to the Euclidean distance of the vector, as in Equation 13, where x is the vector of the difference image and n is the number of data points in that vector.

$$\|x\|_2 = \left(\sum_{i=1}^{n} |x_i|^2\right)^{1/2} \quad \text{Eq. (13)}$$

The normalization step can make it easier to compare the magnitude of the difference-images. Following the normalization step, the standard deviation of the normalized image vector is calculated; this metric is an indication of how similar the background and sample images are. Table 6 shows the standard deviations considered ideal, preferred and acceptable for the spatial distribution of similar backgrounds. Table 7 shows the same metrics for angular distribution.

TABLE 6

| Level of Similarity | Spatial Similarity Metric (Standard Deviation) |
|---|---|
| Acceptable | 0.079 |
| Preferred | 0.052 |
| Ideal | 0 |

TABLE 7

| Level of Similarity | Angular Similarity Metric (Standard Deviation) |
|---|---|
| Acceptable | 0.051 |
| Preferred | 0.036 |
| Ideal | 0 |

An OSRS can capture the current instrument state such that the effect of instrumental and environmental variation on prediction capability can be reduced or eliminated. There are several different methodologies by which the reference spectrum can be used to correct for instrumental and environmental variation, including, but not limited to, those described below.

Correction methodologies can be classed into two broad categories: methods that modify the spectrum of the test sample, and methods that modify the calibration model. A simple method modifies the spectrum of the sample of interest by subtracting the optically similar reference spectrum in absorbance space. The reference spectrum can be the most recently collected optically similar reference spectrum, or it can be a combined spectrum containing information from several background samples collected at different points in time. One method of combining is to exponentially time weight the background reference spectra and average them together. The exponentially time weighted method achieves high signal-to-noise-ratio (by combining multiple spectra) and capturing the current instrument state (by the exponential weightings).

Other background correction methodologies modify the multivariate calibration model. One simple method includes the reference spectra with the original calibration samples and reruns the regression algorithm on the combined data set. Another method includes only the spectral variation from the OSRS in the calibration model. This method takes multiple background reference samples during the calibration period, finds the mean of the background reference sample spectra collected during the calibration period, subtracts (in absorbance space) this mean background reference spectrum from subsequent background reference spectra collected prior to making an actual prediction, adds this spectral difference back to the calibration samples, and reruns the regression algorithm to create an updated calibration model. An alternative method runs an eigenvector decomposition on the spectral differences seen in the background and uses a limited number of eigenvectors to add this spectral variation back to the model.

The metrics for quantifying spectroscopic similarity above are representative; the proper similarity metric for a specific application can depend upon the nature of the errors one seeks to minimize. For example, if errors associated with the distribution of photon pathlengths through the sample of interest are most problematic, a similarity metric might involve a comparison of the experimentally-measured or theoretically-calculated scattering coefficients and/or scattering phase functions of the OSRS and the sample of interest. It is also possible that the proper metric will be some weighted combination of the absorption and scattering properties of these media.

Each of the OSRS embodiments discussed with reference to FIGS. 5–10 can be used in combination with an infrared spectrometer 550 having an illumination source 530 and a collection system 540 as disclosed in U.S. Pat. No. 4,975,581 to Robinson et al., entitled "Method of and Apparatus for Determining the Similarity of a Biological Analyte from a Model Constructed from Known Biological Fluids", incorporated herein by reference. Also, each of the OSRS embodiments can be used in combination with a calibration model (not shown), a suitable example of which is disclosed in U.S. Pat. No. 6,157,041, entitled "Methods and Apparatus for Tailoring Spectroscopic Calibration Models", incorporated herein by reference.

EXAMPLE EMBODIMENTS

Detailed descriptions of several specific embodiments of the present invention are provided below with reference to FIGS. 5–10. These specific OSRSes are useful, for example, in applications in which tissue properties such as analyte concentrations are to be measured in vivo using reflection spectroscopy. Specifically, these OSRSes match the optical properties of tissue at selected wavelengths in the near-infrared region including 4,000 cm$^{-1}$ to 8,000 cm$^{-1}$. In this optical region, water is the dominant absorbing component contained in the tissue. Each of the example OSRS embodiments provides multiple optical pathlengths through water in order to mimic the scattering of living tissue. A distribution of pathlengths can be calculated based upon Monte Carlo simulations of light propagation through scattering media having scattering properties that match those of tissue. The results can be defined by a mean pathlength with a standard deviation and skew to the distribution. The distribution skew is toward longer pathlengths. Typically the standard deviation is less than or equal to the mean. For example, if the mean pathlength is 1 mm, then the standard deviation of pathlengths is about 1 mm as well.

In developing and assessing reference samples, a metric that enables rapid and easy determination if multiple optical pathlengths of water are created by the reference sample can be useful. One simple way is to fit the absorbance spectrum of the reference sample with three terms: 1) an offset, 2) a slope with wavenumber, and 3) the pure component of water. The pure component of water is simply the absorbance of water at a fixed pathlength, mathematically stated in Equation 14.

$$\hat{A}(x) = b_0 + b_1 x + b_2 PC(x) \quad \text{Eq. (14)}$$

The three fitting parameters can be estimated using a least squares fit of Equation 14 to the measured absorbance spectrum. Following fitting of the above parameters the spectral residual is determined. The spectral residual is determined by subtracting the above equation from the absorbance spectrum, A, of the reference sample. The final step is to compute the root-mean-squared (RMS) error of the spectral residual.

$$\text{Multipath\_RMSError} = \sqrt{\frac{1}{N}\sum_{i=1}^{N}(A_i - \hat{A}_i)^2} \qquad \text{Eq. (15)}$$

The multipath RMS error is greater when multiple pathlengths of water are present in the reference sample. A simple threshold value calculated in absorbance units can be used to determine if multiple pathlengths of water are present. The threshold is sensitive to the spectral region used. For example, the threshold will be smaller if the region used for analysis had smaller absorbance bands.

Novel OSRS designs are presented for achieving the multiple water pathlengths desired to match the spectrum of tissue. Embodiments can consist of an optical interface (e.g., an $MgF_2$ window or light guide) that is highly transmissive in the optical region of interest, an optical sampling compartment containing water, and diffusely reflective or scattering media. Experimental and simulated data are presented showing the spectral match between the OSRSes and human tissue.

These OSRS embodiments are examples of embodiments of similar references for the specific application of measuring in vivo tissue characteristics such as analyte concentrations in a particular optical region. Other optical regions or in vitro applications can require substantially different OSRS embodiments. In addition to including the dominant absorbing species (e.g., water), the OSRS can also include one or more analytes of interest (e.g., glucose, ethanol, urea, etc.). By including one or more analytes, the reference sample can be used as a quality control or calibration sample in addition to its use in the maintenance of calibration.

The OSRS examples presented can include a gelling agent such as hydroxyethylcellulose (HEC) or polyvinyl alcohol (PVA), a scattering agent (e.g., scattering particles such as polystyrene beads), water and, optionally, a viscosity controlling agent such as sodium lauryl sulfate. The gelling agent provides a polymer matrix for suspending the scattering particles described below, and provides a matrix for displacing water. HEC can be present in the reference gel formulations from 30,000 to 40,000 mg/dL, or 32,000 to 35,000 mg/dL, or 32,000 mg/dL or 35,000 mg/dL. HEC is commercially available from Hercules, Inc., under the trade name Natrosol HEC 250 LR. A scattering agent can be anything that that scatters light, examples including meshes, three-dimensional structures, particles, and filaments. For convenience, the examples below refer to particles; those skilled in the art will appreciate other scattering agents. Polystyrene beads can be suspended in the HEC matrix and provide the appropriate level of light scattering and bulk absorbtion of light similar to tissue. However, any particles that have a different refractive index than that of the gelling agent and water can be suitable. Other example OSRSes combine scattering solutions with hydrophilic monomers and associated reagents, and then have a polymeric gel formed in a subsequent step.

Polystyrene beads are suitable for use as scattering elements as polystyrene spheres of specific dimensions vary little and are commercially available. This uniform particle dimension of polystyrene provides a homogeneous matrix. Polystyrene beads can have any diameter and be present in any concentration sufficient to simulate the spectral properties of tissue.

Polystyrene beads can have a diameter of 0.2 to 10 μm, or 0.8 to 1 μm, or 0.9 to 0.95 μm, or 0.93 μm. The polystyrene beads included in the OSRS can include beads of one or more diameters. For example, a first set of beads having a first diameter and a second group of beads having a second diameter different than the first diameter can be present. A third group of beads having a third diameter different from the first and second diameters can also be present. A fourth group of polystyrene beads having a fourth diameter different than the first, second or third diameters can also be present.

A first group of polystyrene beads can have a first diameter of 0.14 to 0.35 μm or 0.3 μm and be present in the composition at a concentration of from 150 to 250 mg/dL or 170 mg/dL or 200 mg/dL. A second group of polystyrene beads can have a diameter of 0.8 to 1 μm, or 0.9 to 0.95 μm, or 0.93 μm and be present in the composition at a concentration of 1400 to 1800 mg/dL, or 1600 mg/dL, or 900 to 950 mg/dL, or 940 mg/dL, or 920 mg/dL. A third group of polystyrene beads can have a diameter of 5 to 6 μm, or 5.3 to 5.7 μm or 5.5 μm and be present in the composition at a concentration of 50 to 350 mg/dL, or 90 mg/dL, or 310 mg/dL. A fourth group of polystyrene beads can have a fourth diameter of 6 to 7 μm, 6.2 to 6.5 μm, or 6.3 μm and be present in the composition at a concentration of 250 to 700 mg/dL, or 300 mg/dL, or 640 mg/dL.

The composition can include an overall concentration of polystyrene beads of 1300 to 2300 mg/dL or 1400 to 1800 mg/dL, or 1700 mg/dL, or 1850 mg/dL.

Water can be present in the composition at a ratio of 30 weight % HEC to 70 weight % water. The concentration of water in the composition can be 60,000 to 85,000 mg/dL or 70,000 to 80,000 mg/dL or 75,000 to 80,000 mg/dL or 70,000 mg/dL or 75,000 mg/dL or 77,000 mg/dL.

Sodium lauryl sulfate, also known as sodium dodecyl sulfate, can be present in the composition from 100 to 5,000 mg/dL, or 1,000 to 4,000 mg/dL, or 1,000 mg/dL; or 4,000 mg/dL, or 500 to 1,500 mg/dL. Sodium lauryl sulfate can serve as a surfactant, lowering the viscosity of the hydroethycellulose and allowing concentrated gels. Sodium lauryl sulfate is commercially available as J. T. Baker's sodium dodecyl sulfate. Other materials can provide similar effects. See, e.g., Natrosol Hydroxyethylcellulose, Physical and Chemical Properties from Aqualon, incorporated herein by reference.

Example OSRS

Figure 5:
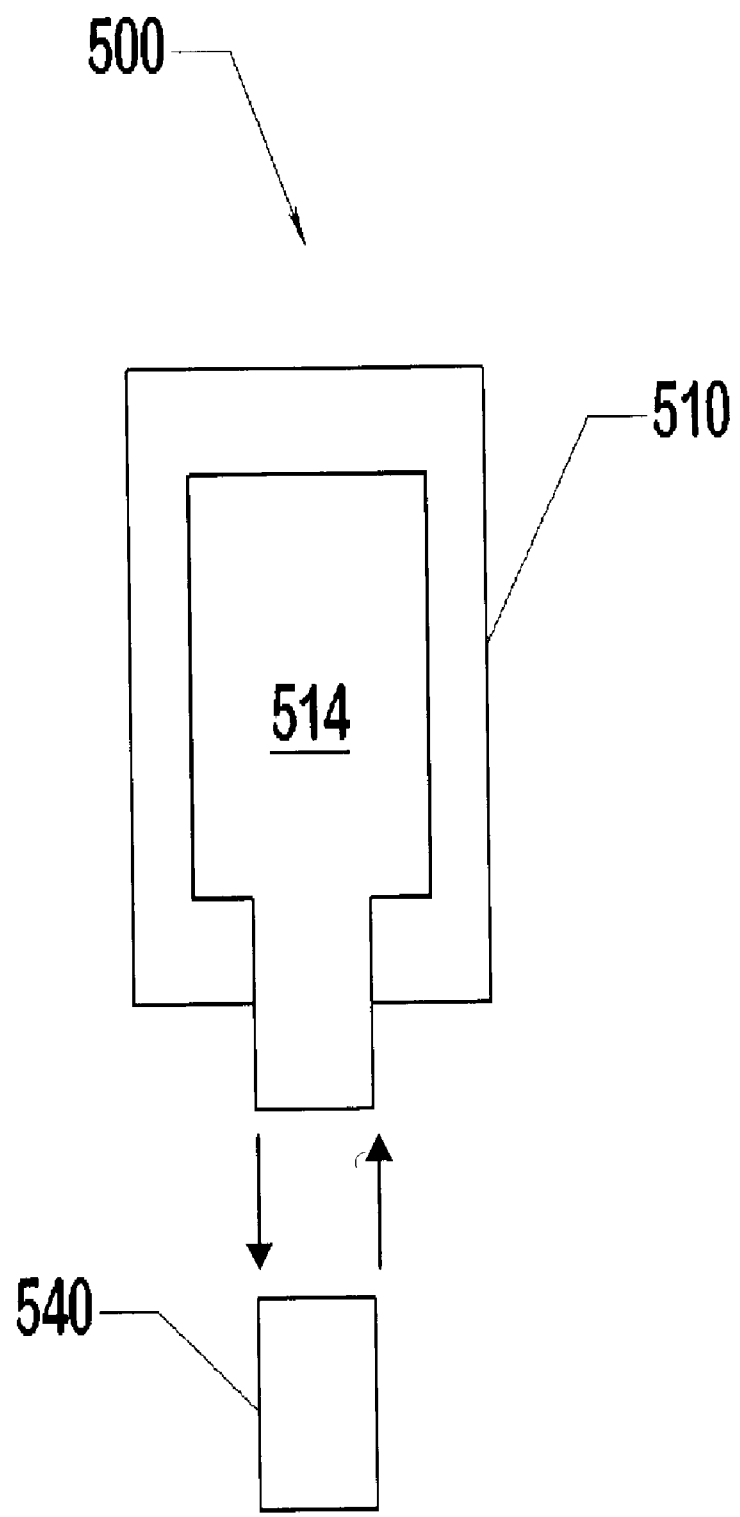
FIG. 5 is a schematic illustration of an OSRS in accordance with an embodiment of the present invention.
Figure 6:
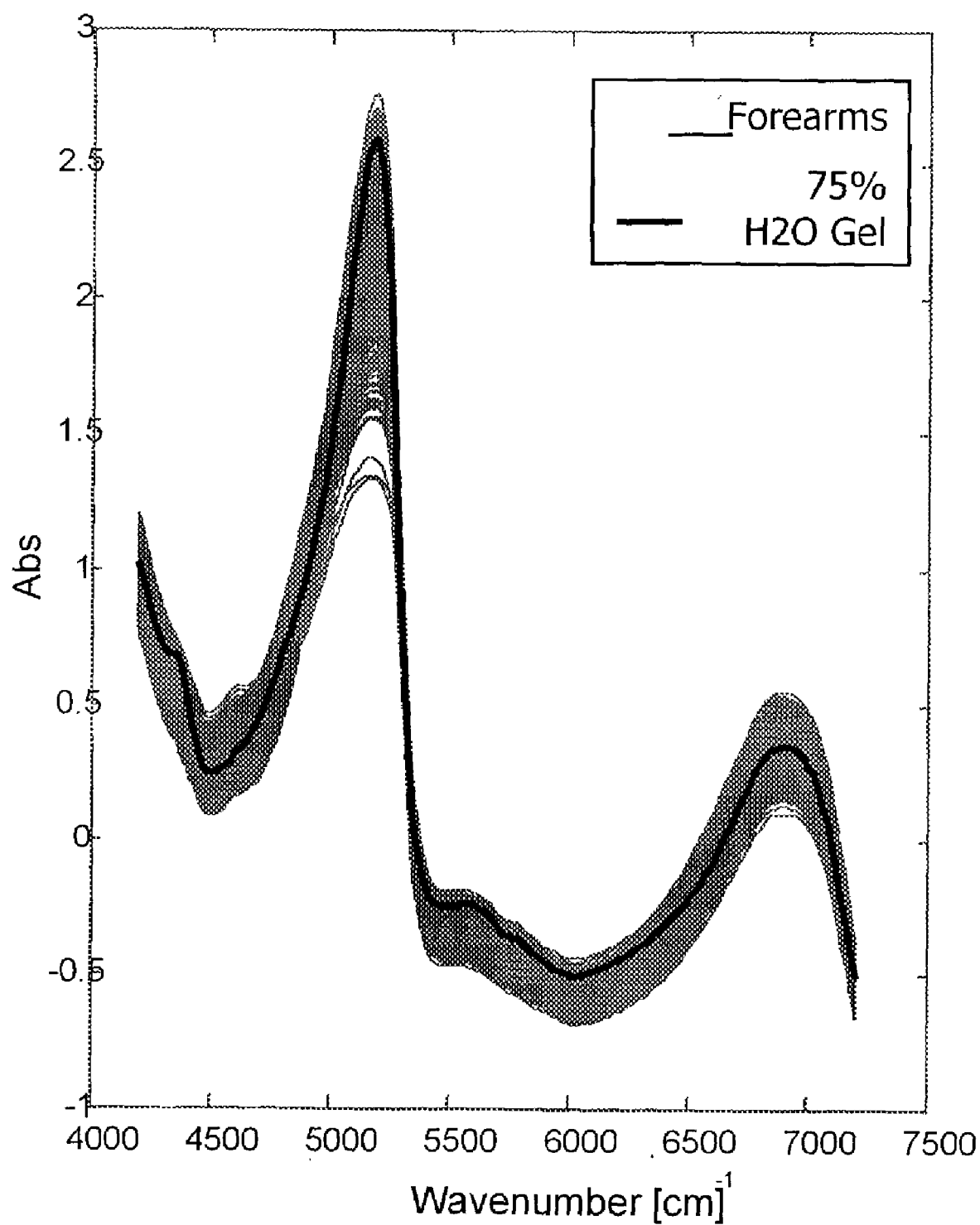
FIG. 6 is a graph of spectral response demonstrating the spectral match between the tissue sample and an OSRS.

FIG. 5 is a schematic illustration of an OSRS 500 in accordance with an embodiment of the present invention. The OSRS 500 includes a container 510, approximately 10 mm×13mm, that is partially optically transparent. A reference gel 514 is disposed in the container and comprises a reference gel formulation like those described herein. FIG. 6 is a graph of spectral response demonstrating the spectral match between the tissue sample spectrum and the reference gel spectrum 500. The reference gel thickness presented to the sampling system 540 was 3 cm to 4 cm. As can be seen from FIG. 6, a close match to human tissue can be made if the proper preparation of the reference gel is carried out as shown in the examples. The reference gel can comprise any substance with the required optical characteristics.

Example OSRS

Figure 7A:
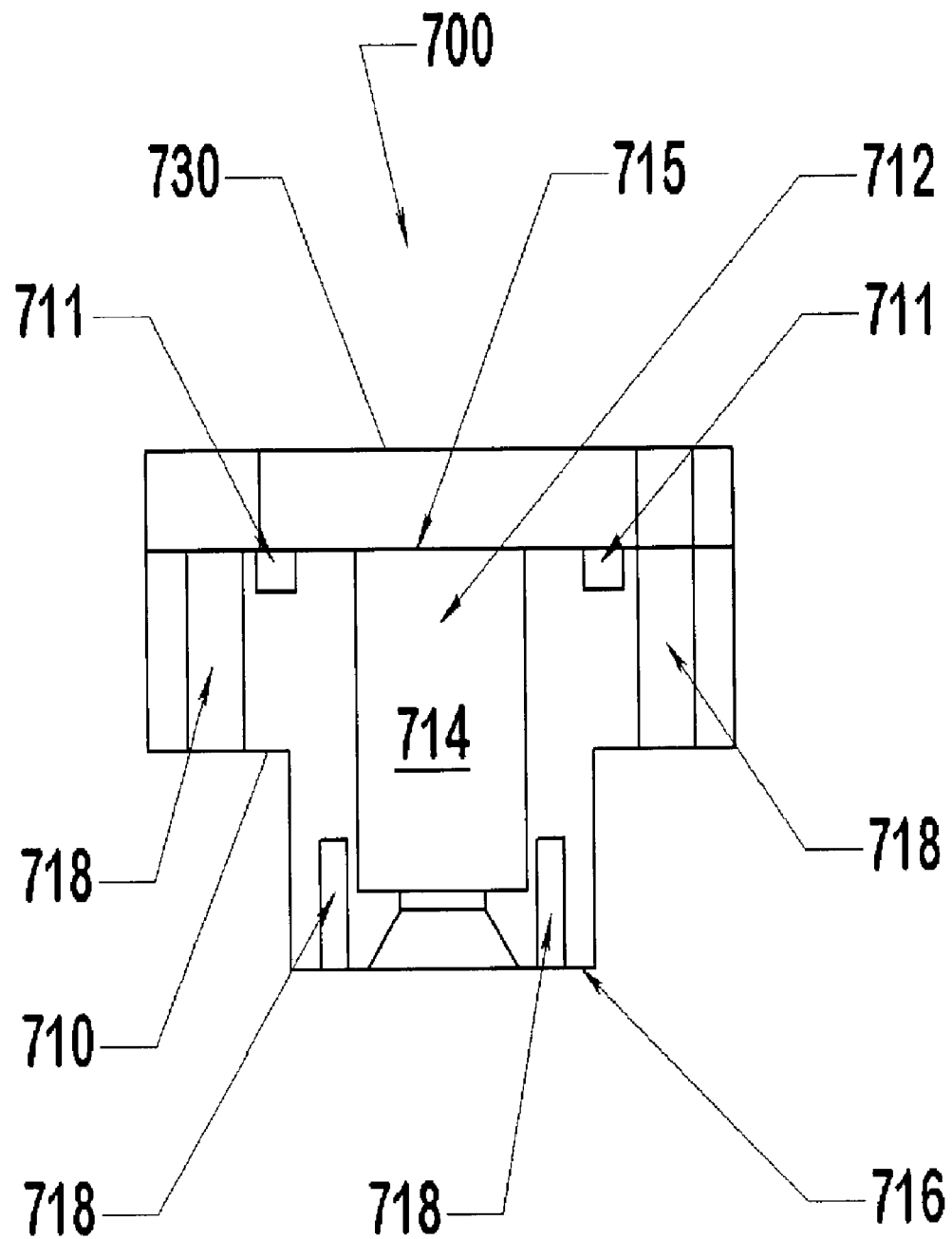
FIG. 7A is a cross-section end elevation view of a main body portion of a reference gel container shown in FIG. 7C in accordance with an embodiment of the invention.

FIGS. 7A to 7D show an embodiment of an OSRS according to the present invention comprising a reference gel container 700. FIG. 7A is a cross-section view of a main body portion 710 of a reference gel container 700 shown in FIG. 7C in accordance with an embodiment of the invention. Main body 710 defines an inner reference gel cavity 712 where a reference gel 714 can be disposed. The main body 710 can include a plurality of fastening holes 718 for fastening a top plate 730 and/or a light guide holder 724 to the main body 710, where the light guide holder is adapted to mount a light guide accommodating light transmission to and from the OSRS. The main body 710 can also include a gasket groove 711 disposed on either a top surface 715 or a bottom surface 716 of the main body 710. The gasket groove 711 can surround the inner reference gel cavity 712. The inner reference gel cavity 712 can extend substantially through the main body 710. The light guide cavity 713 can be continuous with the inner reference gel cavity 712.

Figure 7B:
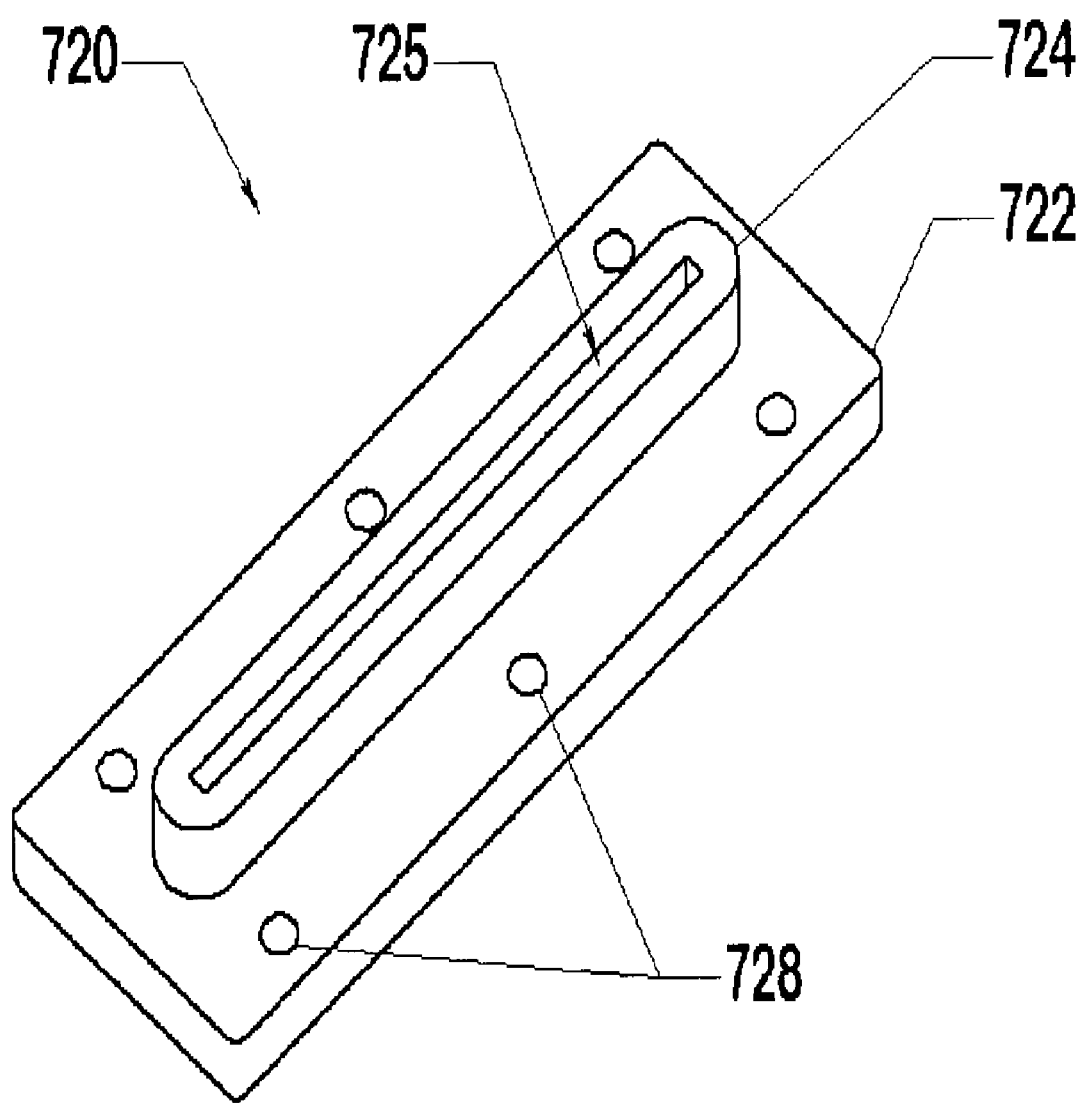
FIG. 7B is a perspective view of a bottom plate of a reference gel container shown in FIG. 7C in accordance with an embodiment of the invention.

FIG. 7B is a perspective view of a bottom plate 720 of a reference gel container 700. The bottom plate 720 can include a light guide holder 724 which extends upwardly from the bottom plate 720, the light guide holder 724 defines a light guide cavity 725 that extends through the light guide holder 724 and the bottom plate 720. A light guide (not shown) can be disposed within the light guide cavity 725. The bottom plate 720 can include a fastening flange 722 that may extend perpendicular from the light guide holder 724. The fastening flange 722 can include one or more fastening holes 728. The bottom plate 720 can be fastened to the main body 710 at the bottom surface 716 of the main body 710.

Figure 7C:
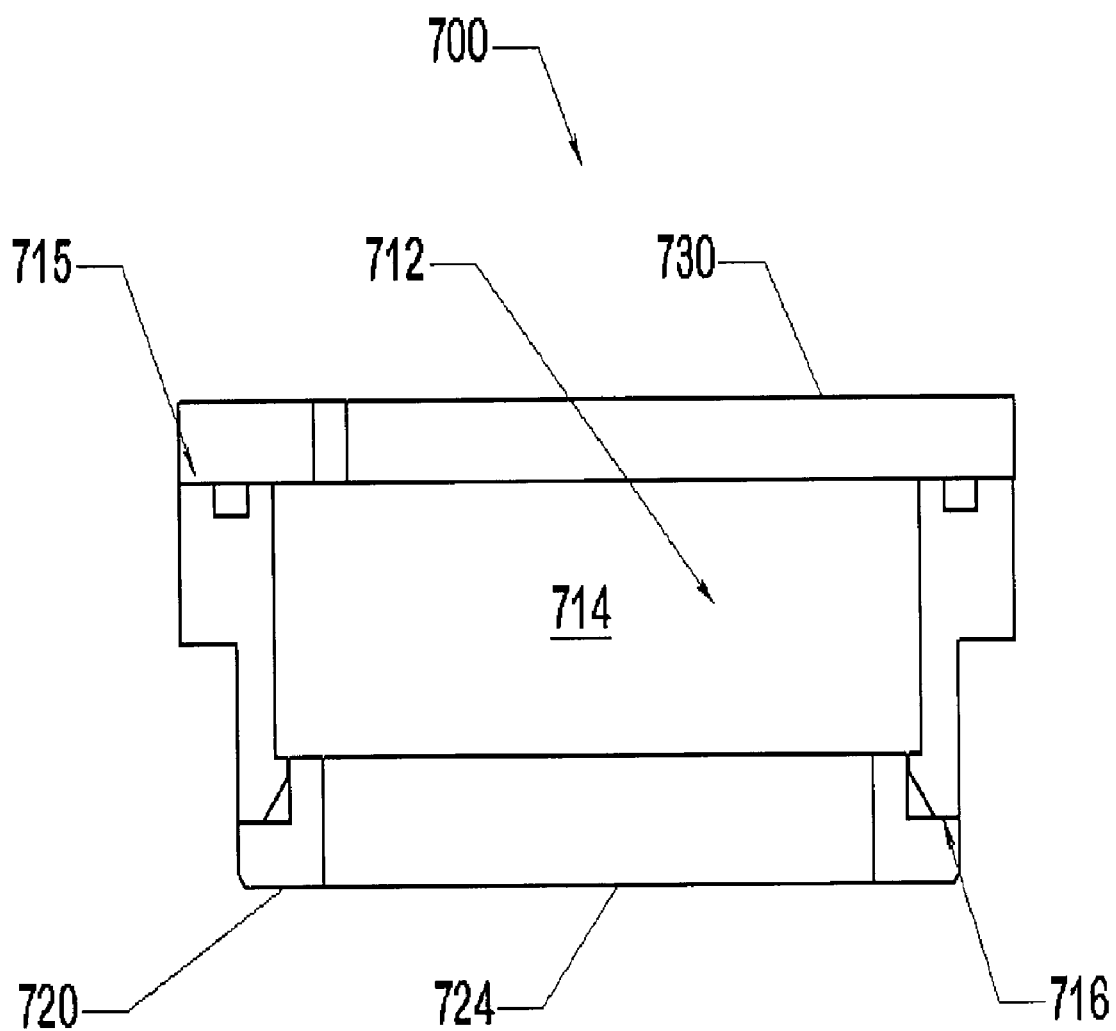
FIG. 7C is a cross-section side elevation view of a reference gel container in accordance with an embodiment of the invention.

FIG. 7C is a cross section view of a reference gel container 700. The gel reference container 700 is assembled by mounting the bottom plate 720 with the bottom surface 716 of the main body 710 and mounting a top plate 730 with a top surface 715 of the main body 710. The reference gel 714 is located between the top plate 730 and the light guide holder 724 in the reference gel cavity 712 such that the light guide (not shown) is proximate to the reference gel 714.

Figure 7D:
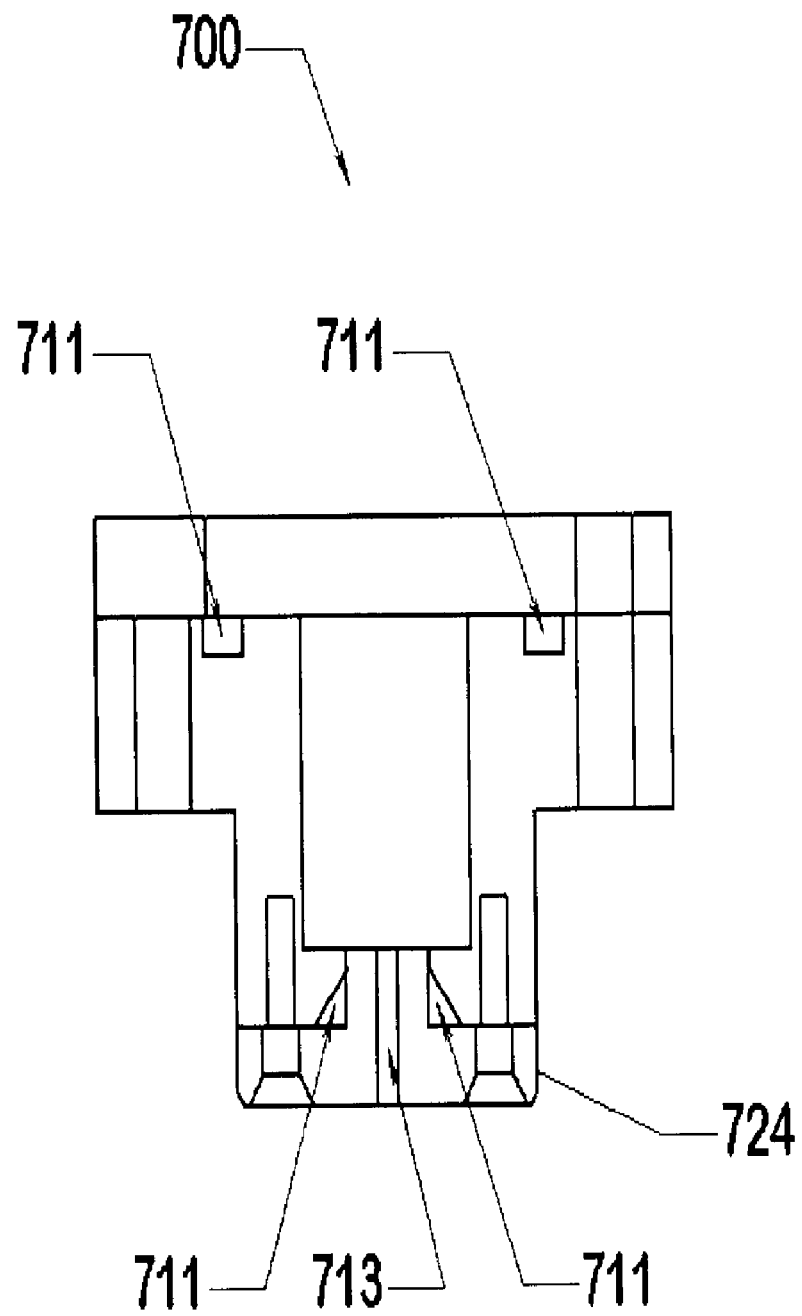
FIG. 7D is a cross-section end elevation view of the reference gel container shown in FIG. 7C in accordance with an embodiment of the invention.

FIG. 7D is a cross sectional view of the reference gel container 700 shown in FIG. 7C. A light guide (not shown) disposed within the reference gel container 700 can extend from an outer surface of the reference gel container to the inner reference gel cavity surface. The reference gel container 700 can also include a gasket (not shown) disposed within gasket groove 711.

Example OSRS

Figure 8A:
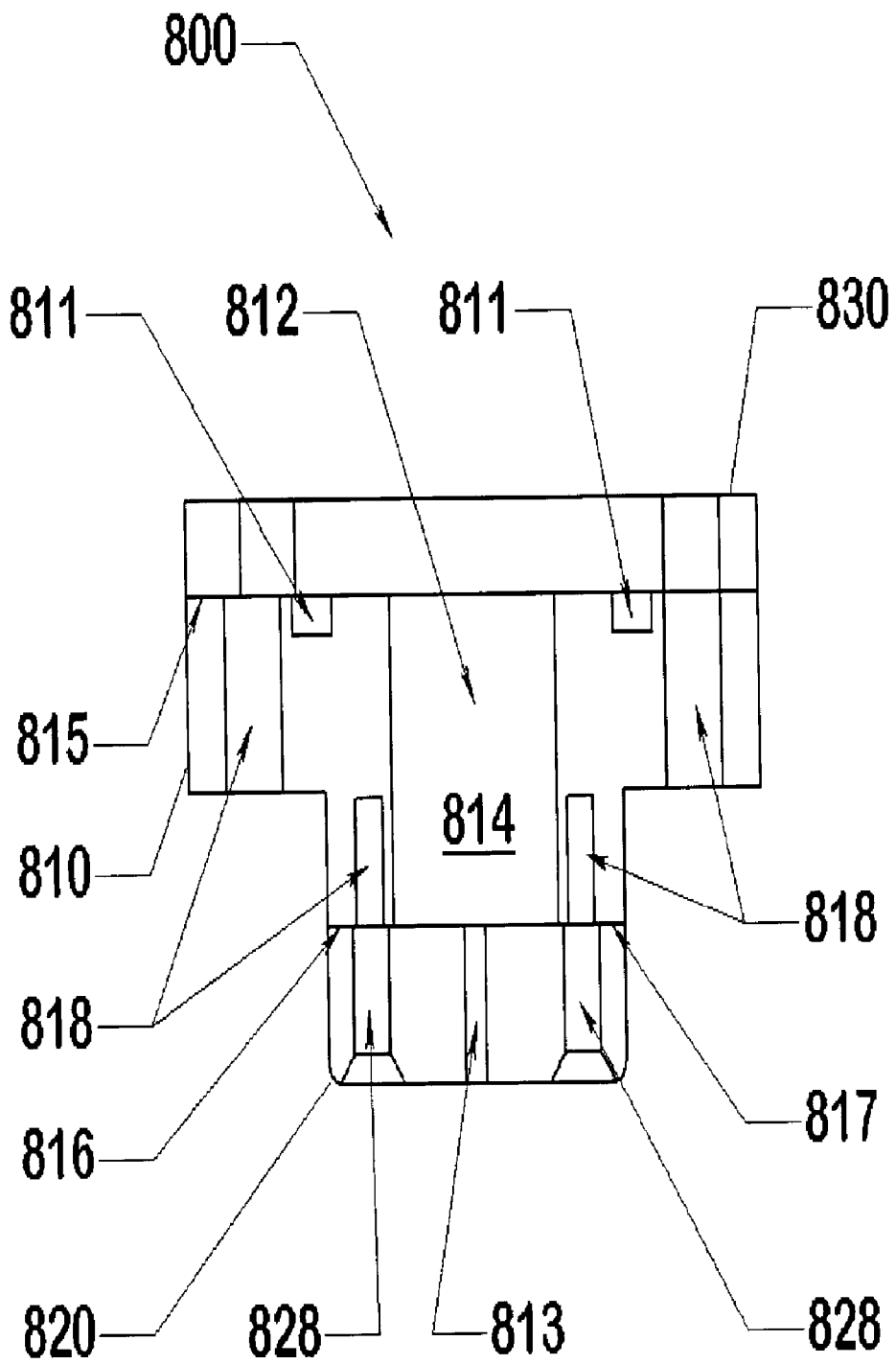
FIG. 8A is a cross-section end elevation view of the reference gel container shown in FIG. 8B in accordance with an embodiment of the invention.
Figure 8B:
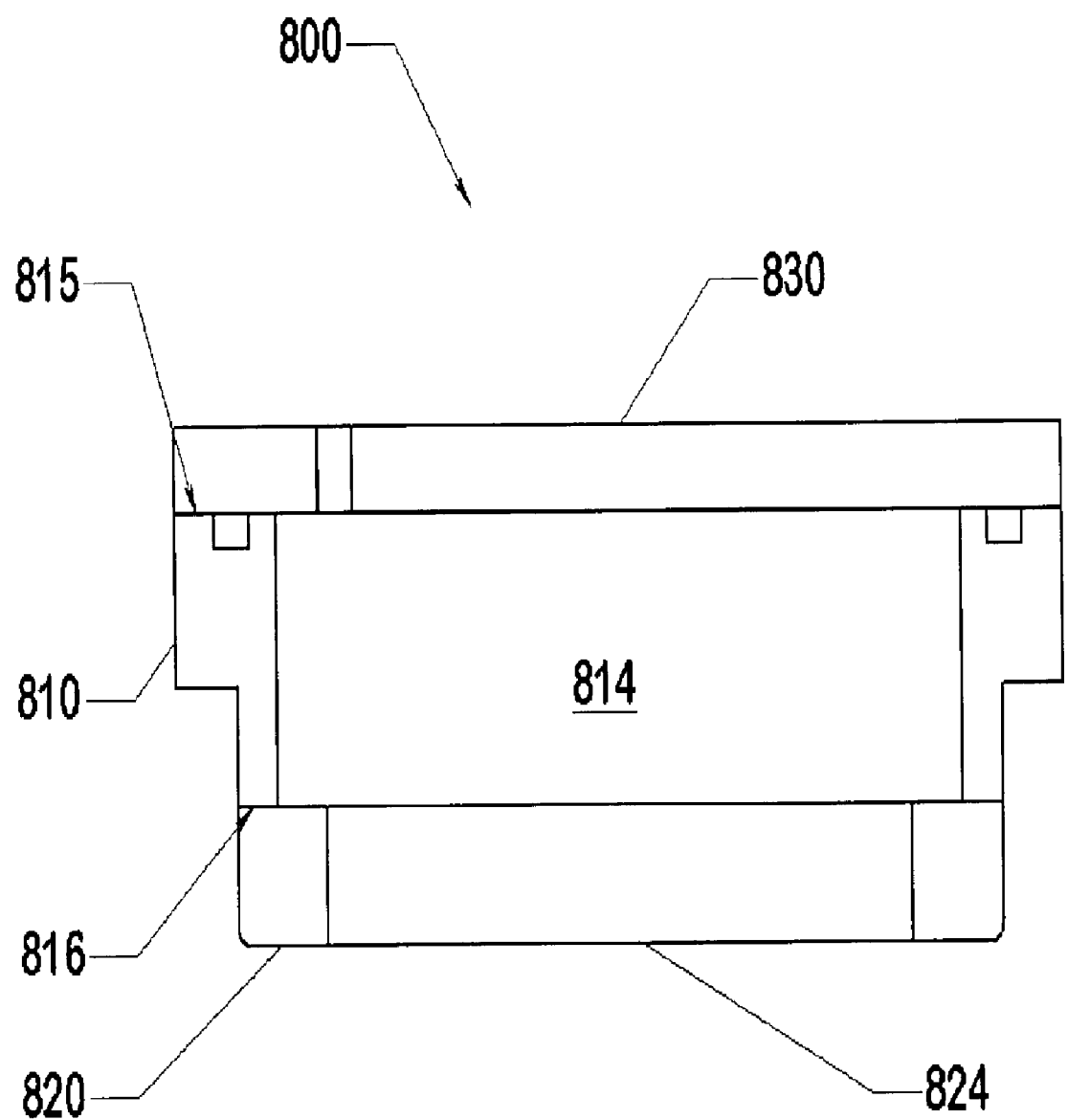
FIG. 8B is a cross-section side elevation view of a reference gel container in accordance with an embodiment of the invention.

FIGS. 8A to 8B show an embodiment of an OSRS according to the present invention, comprising a reference gel container. FIG. 8A is a cross-sectional end elevation view of the reference gel container 800 shown in FIG. 8B. A main body portion 810 defines an inner reference gel cavity 812 where a reference gel 814 can be disposed. The main body 810 can include a plurality of fastening holes 818 for fastening a top plate 830 and/or a light guide holder 824 to the main body 810. The main body 810 can also include a gasket groove 811 disposed on a top surface 815 of the main body 810. The gasket groove 811 can surround the inner reference gel cavity 812. The inner reference gel cavity 812 can extend substantially through the main body 810. A light guide cavity 813 can be located on the bottom surface 816 of the main body 810. The light guide cavity 813 can be continuous with the inner reference gel cavity 812. A bottom plate 820 can include a light guide holder 824 which is integral with the bottom plate 820 and has a substantially a flat surface mating surface 817 for mating with the bottom surface 816. The light guide holder 824 defines a light guide cavity 813 that extends through the light guide holder 824. A light guide (not shown) can be disposed within the light guide cavity 813. The bottom plate 820 can include one or more fastening holes 828. The bottom plate 820 can be fastened to the main body 810 at the bottom surface 816 of the main body 810. The light guide disposed within the reference gel container 800 extends from an outer surface of the gel reference container to the inner reference gel cavity surface. The reference gel container 800 can also include a gasket (not shown) disposed within the gasket groove 811. The top plate 830 can be secured to the main body 810 with a sealant, such as, for example an epoxy. The bottom plate 820 can be secured to the main body 810 with a sealant, such as, for example an epoxy.

FIG. 8B is a cross section view of a reference gel container 800. The reference gel container 800 can be assembled by securing the bottom plate 820 to the bottom surface 816 of the main body 810 and securing a top plate 830 on a top surface 815 of the main body 810. The reference gel 814 is located between the top plate 830 and the light guide holder 824 in the reference gel cavity 812 such that the light guide is proximate to the reference gel 814.

Example OSRS

Figure 9A:
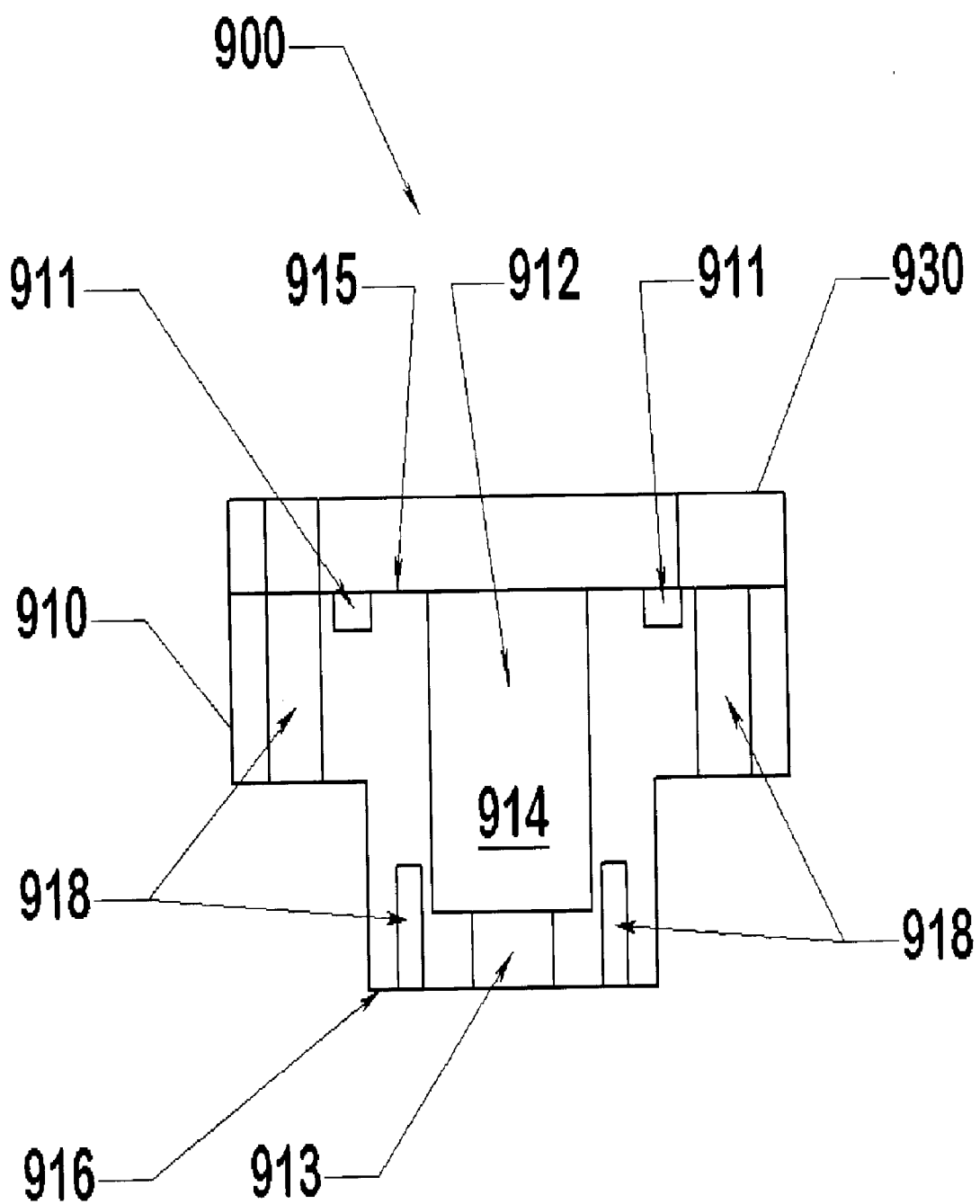
FIG. 9A is a cross-section end elevation view of a main body portion of a reference gel container shown in FIG. 9C in accordance with an embodiment of the invention.

FIGS. 9A to 9D show an embodiment of an OSRS according to the present invention, comprising a reference gel container 900. FIG. 9A is a cross-section and elevation view of a main body portion 910 of a reference gel container 900 shown in FIG. 9C in accordance with an embodiment of the invention. The main body portion 910 defines an inner reference gel cavity 912 where a reference gel 914 can be disposed. The main body 910 can include a plurality of fastening holes 918 for fastening a top plate 930 and/or a light guide holder 924 to the main body 910. The main body 910 can also include a gasket groove 911 disposed on either a top surface 915 or a bottom surface 916 of the main body 910. The gasket groove 911 can surround the inner reference gel cavity 912. The inner reference gel cavity 912 can extend substantially through the main body 910. A light guide cavity 913 can be located on the bottom surface 916 of the main body 910. The light guide cavity 913 can be continuous with the inner reference gel cavity 912.

Figure 9B:
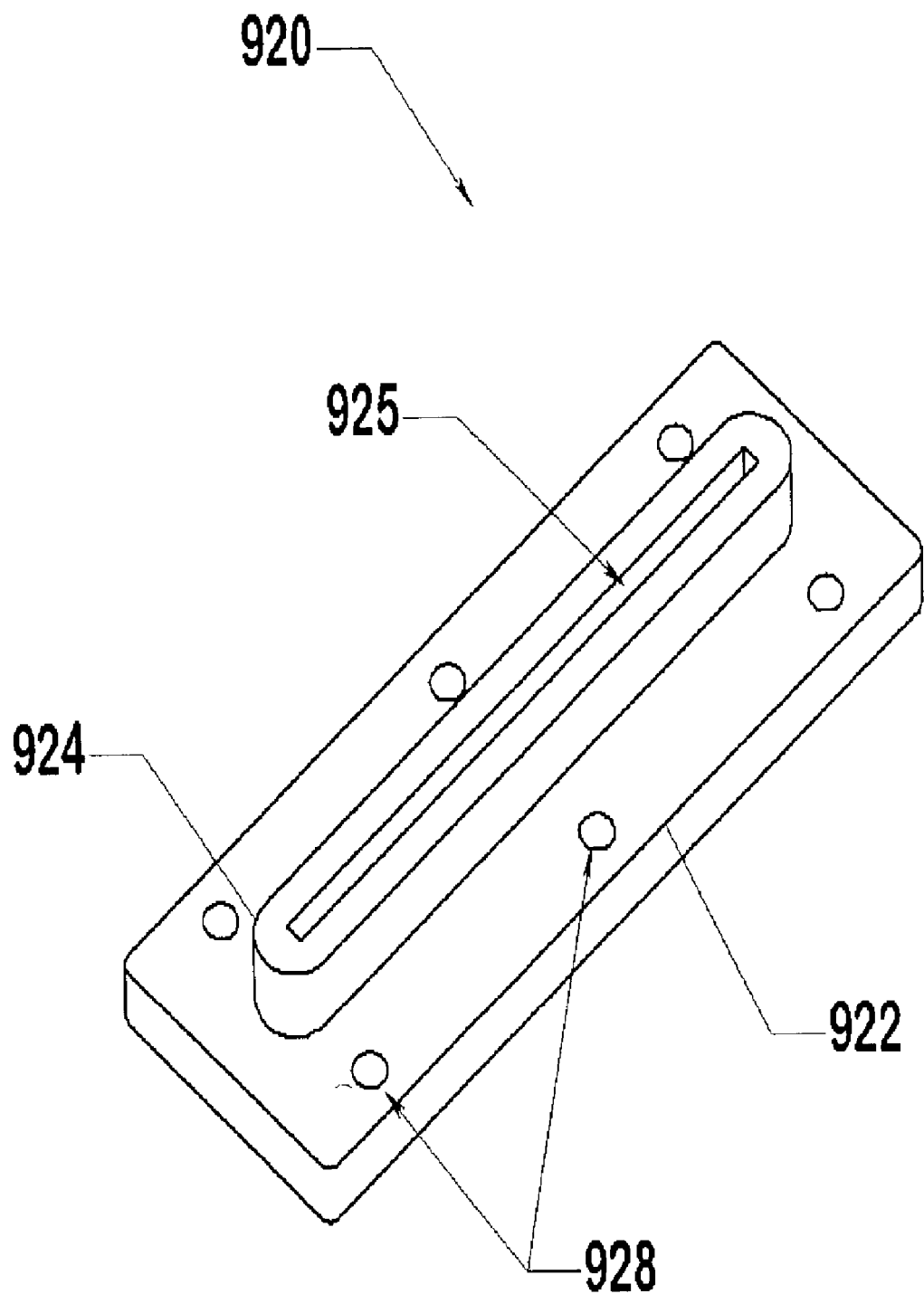
FIG. 9B is a perspective view of a bottom plate of a reference gel container shown in FIG. 9C in accordance with an embodiment of the invention.
Figure 9C:
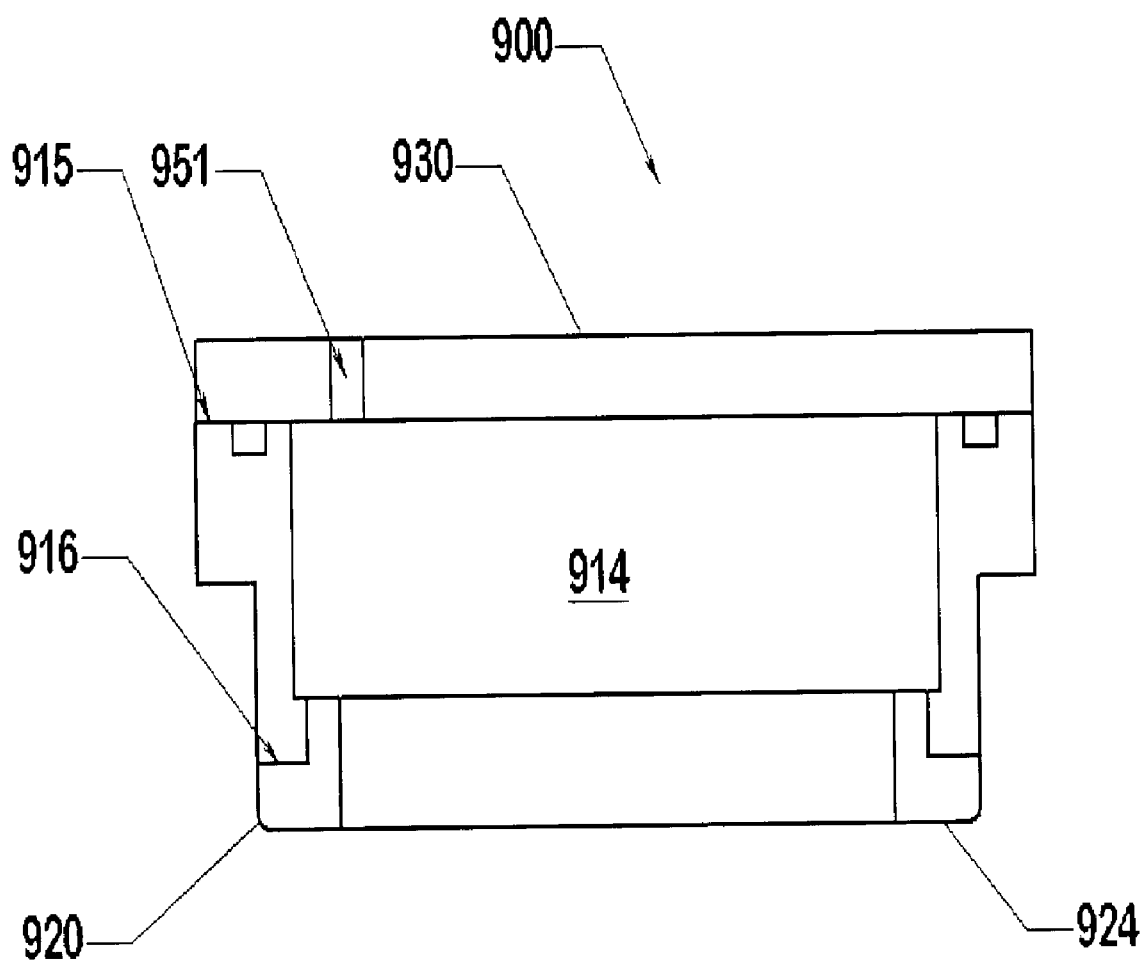
FIG. 9C is a cross-section side elevation view of a reference gel container in accordance with an embodiment of the invention.

FIG. 9B is a perspective view of a bottom plate 920 of a reference gel container 900 showing FIG. 9C. The bottom plate 920 can include a light guide holder 924 which extends upwardly from the bottom plate 920, the light guide holder 924 defines a light guide cavity 925 that extends through the light guide holder 924 and the bottom plate 920. A light guide (not shown) can be disposed within the light guide cavity 925. The bottom plate 920 can include a fastening flange 922 that can extend perpendicular from the light guide holder 924. The fastening flange 922 can include one or more fastening holes 928. The bottom plate 920 can be fastened to the main body 910 at the bottom surface 916 of the main body 910.

FIG. 9C is a cross section side elevation view of a reference gel container 900. The reference gel container 900 can be assembled by securing the bottom plate 920 to the bottom surface 916 of the main body 910 and securing a top plate 930 on a top surface 915 of the main body 910. The reference gel 914 is located between the top plate 930 and the light guide holder 924 in the reference gel cavity 912 such that the light guide is proximate to the reference gel 914. Top plate 930 can further define a port 951 to allow evacuation of excess air during assembly.

Figure 9D:
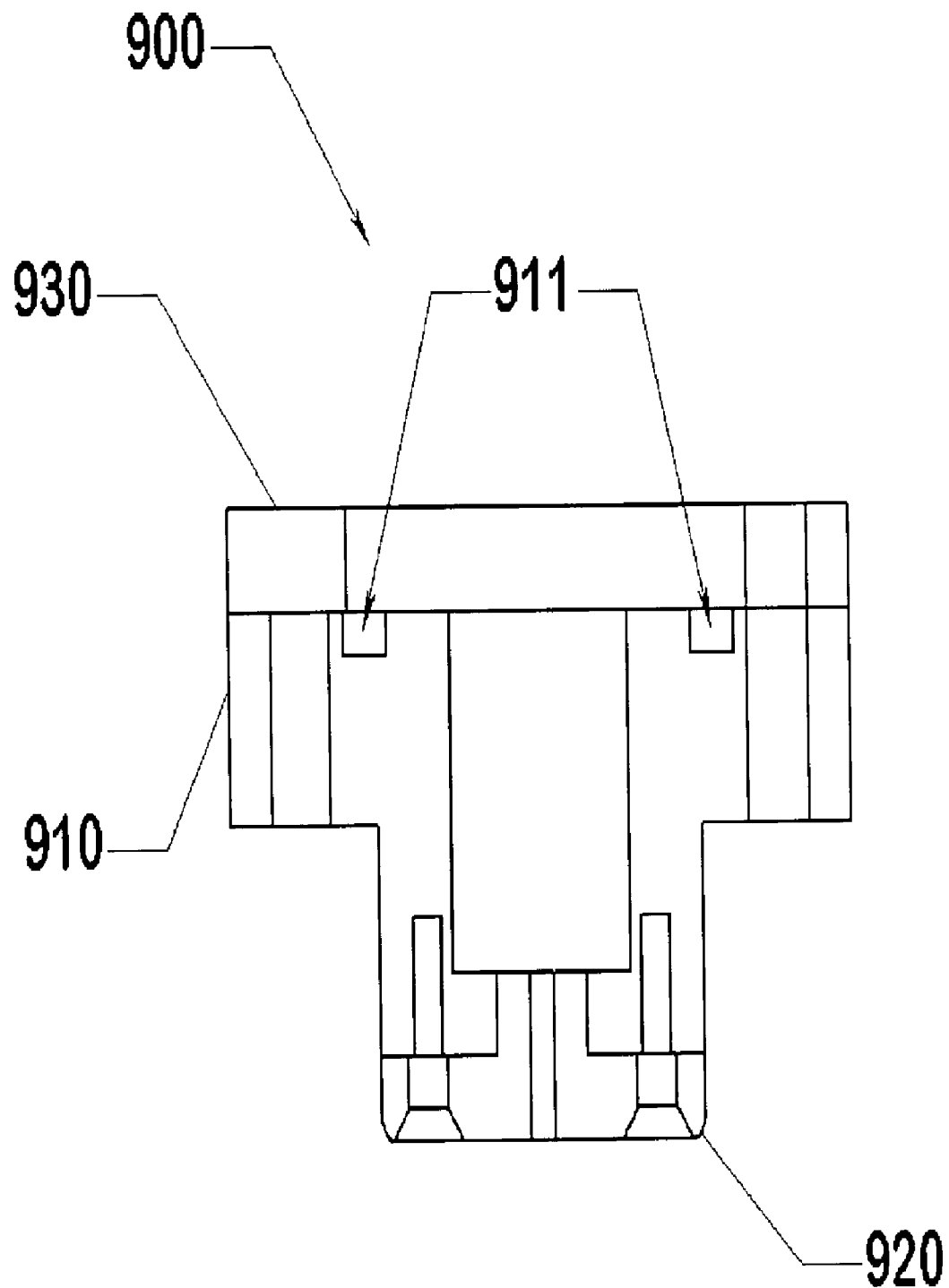
FIG. 9D is a cross-section end elevation view of the reference gel container shown in FIG. 9C in accordance with an embodiment of the invention.

FIG. 9D is a cross sectional end elevation view of the reference gel container 900 shown in FIG. 9C. A light guide disposed within the reference gel container 900 can extend from an outer surface of the reference gel container 927 to the inner reference gel cavity surface 925. The reference gel container 900 can also include a gasket (not shown) disposed within the gasket groove 911. The top plate 930 can be secured to the main body 910 with a sealant, such as, for example an epoxy. The bottom plate 920 can be secured to the main body 910 with a sealant, such as, for example an epoxy.

Example OSRS

Figure 10A:
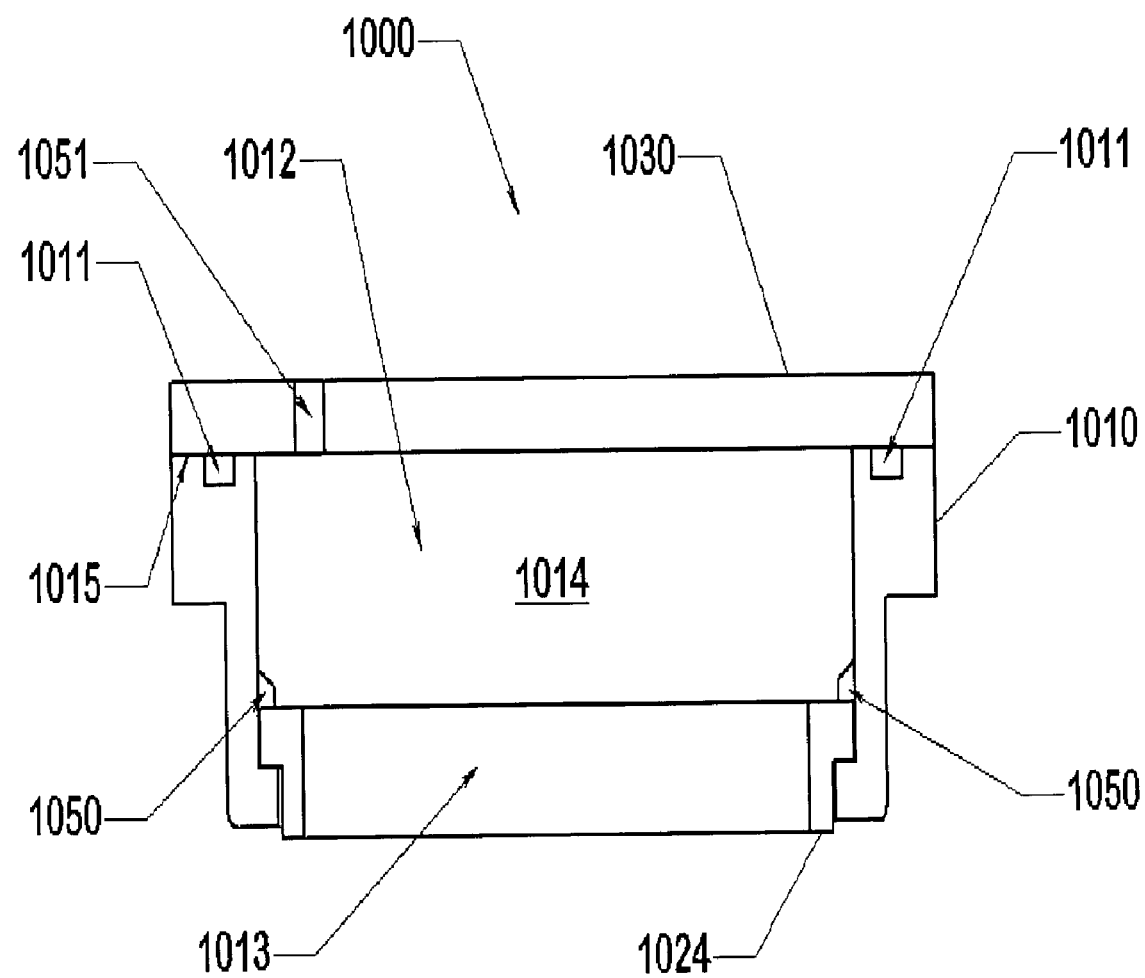
FIG. 10A is a cross-section side elevation view of a reference gel container in accordance with an embodiment of the invention.
Figure 10B:
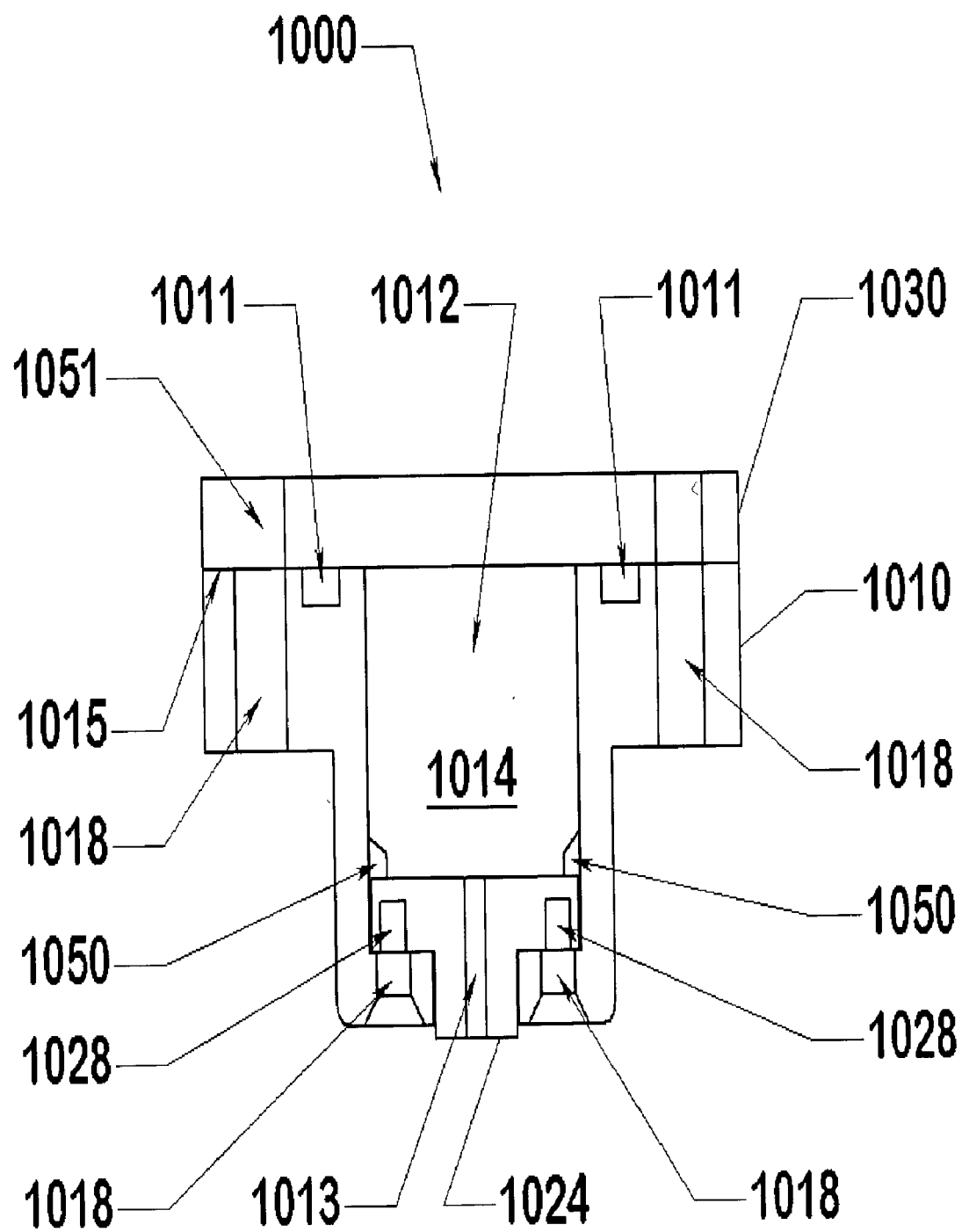
FIG. 10B is a cross-section end elevation view of the reference gel container shown in FIG. 10A in accordance with an embodiment of the invention.

FIGS. 10A to 10B show an embodiment of an OSRS according to the present invention, comprising a reference gel container 1000. FIG. 10B is a cross sectional end elevation view of the reference gel container 1000 shown in FIG. 10A. A main body portion 1010 defines an inner reference gel cavity 1012 where a reference gel 1014 may be disposed. The main body 1010 can include a plurality of fastening holes 1018 for fastening a top plate 1030 and/or a light guide holder 1024 to the main body 1010. The main body 1010 can also include a gasket groove 1011 disposed on a top surface 1015 of the main body 1010. The gasket groove 1011 can surround the inner reference gel cavity 1012. The inner reference gel cavity 1012 can extend substantially through the main body 1010. A light guide holder 1024 defines a light guide cavity 1013 that extends through the light guide holder 1024. The light guide cavity 1013 can be continuous with the inner reference gel cavity 1012. A light guide (not shown) can be disposed within the light guide cavity 1013. The light guide holder 1024 can include one or more fastening holes 1028. A light guide disposed within the reference gel container 1000 can extend from an outer surface of the gel reference container 1027 to the inner reference gel cavity surface 1025. The reference gel container 1000 can also include a gasket (not shown) disposed within the gasket groove 1011. The top plate 1030 can be secured to the main body 1010 with a sealant, such as, for example an epoxy. The light guide holder 1024 can be secured to the main body 1010 with a sealant 1050, such as, for example an epoxy. Top plate 1030 can further define a port 1051 to allow evacuation of excess air during assembly.

FIG. 10B is a cross section view of a reference gel container 1000. The reference gel container 1000 can be assembled by securing the light guide holder 1024 to the main body 1010 at the inner reference gel cavity surface 1025 and light guide cavity surface 1013 and securing a top plate 1030 on a top surface 1015 of the main body 1010. The reference gel 1014 is located between the top plate 1030 and the light guide holder 1024 in the reference gel cavity 1012 such that the light guide (not shown) is proximate to the reference gel 1014.

An OSRS according to the present invention can also be applied directly to a sampler, without first encapsulating in a carrier. The composition, thickness, and temperature of the OSRS, as well as the application method can be designed to accommodate the instrument and performance desired. Lubricants and index matching materials can also be used in accommodating such direct application. As an example, the OSRS can be shaped to present a convex surface to the sampler, so that, when applied to the sampler, the OSRS material reduces the possibility of trapped air which might degrade the interface. Control of the viscosity can foster an OSRS material that retains its shape sufficient for application, while remaining compliant for shaping to the sampler interface.

OSRS in Use

All of the OSRSes discussed above can be used in conjunction with an optical spectrometer, which typically includes, among other components, an illumination source and a collection system. The reference sample is optically coupled (e.g., positioned adjacent) to the illumination source and irradiated with multiple wavelengths of radiation from the illumination source. The collection system is used to collect radiation that is not absorbed by the reference sample. The collected radiation is then used to determine the intensities of the non-absorbed radiation at each of the multiple wavelengths to generate a reference spectrum. A new calibration model can be created or a pre-existing calibration model can be modified based on the reference spectrum to account for instrument and environment variations. Alternatively, the reference spectrum is simply used to alter a spectrum of a test sample to account for instrument and environment variations without altering an existing model.

After the calibration model has been created or modified, a test sample of interest is optically coupled (e.g., positioned adjacent) to the illumination source. The test sample (e.g., human tissue or blood) is irradiated with multiple wavelengths of radiation from the illumination source. Radiation that is not absorbed by the test sample is collected with the collection system. The collected radiation is then used to determine the intensities of the non-absorbed radiation at each of the multiple wavelengths to generate a test spectrum corresponding to the test sample of interest. In one embodiment, the newly created or modified calibration model is used, and an analyte or attribute of the test sample may be calculated based on the test spectrum. Alternatively, the test sample spectrum is modified based on the reference spectrum (i.e., a ratio or difference) and the modified test spectrum is used with an existing model to determine an analyte concentration or attribute.

Note that these steps may be reordered and/or modified without departing from the scope of the present invention. For example, the reference sample can have the same or separate interface with the instrument as that used for the test sample of interest. Also, the reference sample can have multiple components that are simultaneously measured at different locations in the optical path of the spectroscopic instrument. Further, the reference sample can be manually or automatically positioned and measured.

In order to correct for time-dependent effects of instrument and environmental variation, the OSRS can preferably be sampled sufficiently close in time to the sample of interest. The required frequency of sampling for the OSRS is dependent on instrument stability and environmental variations. Preferably, an OSRS measurement is made just prior to measuring the sample of interest which allows the most current instrument state to be determined. In an alternative sampling scheme, the signal-to-noise ratio in the measured background spectrum is improved by taking multiple similar background measurements prior to measuring the sample of interest.

There are several schemes for optimizing the relationship between using multiple background sample measurements (higher signal-to-noise) and using only the background sample measurement made closest in time to the measurement of the sample of interest (most current instrument state). One such scheme is to use multiple, weighted, time-averaged background sample measurements. Multiple background sample measurements are collected over a period of time in order to increase the spectrum's signal-to-noise ratio. Weighted averaging allows those background sample spectra taken closest in time to the sample of interest to more heavily influence the spectral correction.

There are multiple methods for using the spectral measurement of the OSRS to correct for instrument and environmental variation. One simple and effective methodology is to adjust the measured spectrum of the sample of interest by the measured spectrum of the OSRS. This correction methodology removes spectral variation that is common to both the OSRS and the sample of interest. This methodology can be used to both establish and maintain a multivariate calibration model, but in some cases, it is desirable to use this methodology only for calibration maintenance.

From the foregoing, it will be apparent to those skilled in the art that the present invention provides devices, systems and methods for establishing and/or maintaining the prediction capability over time of a multivariate calibration model designed for quantitative optical spectroscopic measurement of attributes or analytes in bodily tissues, bodily fluids or other biological samples. The present invention is particularly useful when the spectral absorbance of the attribute or analyte is small relative to the background. The present invention provides an OSRS that can capture the characteristics of instrument and environmental variation and reduce the effect of such variation on the measurement capability of the model.

Example Gel Precursor OSRS

A gel precursor OSRS can be made by combining scattering solutions with hydrophilic monomers and associated reagents, and then forming a polymeric gel in a subsequent step. With appropriate reagent choices, this approach can yield a low-viscosity gel precursor that facilitates subsequent sample preparation steps like mixing and degassing. When sample preparation is complete, a copolymerization reaction is initiated to form a covalently-crosslinked gel. This can result in a sample with stable and uniform optical properties.

The gel precursor can comprise a crosslinking agent containing two or more vinyl groups, and, optionally, a monomer containing a vinyl group. These vinyl groups can copolymerize through an addition polymerization when initiated by a free-radical generating system. The monomer can be selected to have water solubility greater than 5% (w/w) in its monomeric and polymeric forms and the ability to undergo vinyl addition polymerization. There are many suitable monomers containing vinyl groups in combination with one or more hydrophilic groups, such as amines, amides, alcohols, lactams, esters, and ethers, which increase the monomer's water solubility. Illustrative examples include acrylamide, 2-hydroxyethyl methacrylate, poly(ethylene glycol) methacrylate and 1-vinyl-2-pyrrolidinone (also called 1-vinyl-2-pyrrolidone and n-vinyl pyrrolidone). (all purchased from Sigma-Adrich).

The crosslinking agent can be selected to have water solubility greater than 0.5% (w/w) in its monomer and polymer forms and have two or more vinyl groups available for addition polymerization. Many of the monomers noted above have crosslinking analogs, which consist of two monomer groups linked by a bridging group. Illustrative examples include N,N'methylenebisacrylamide and ethylene glycol dimethacrylate. Pairing these analogs with their monomer counterparts promotes uniform copolymerization reactions. When monomers and crosslinking agents with different chemical functionality are combined, the resulting copolymers can be examined for homogeneity with spectroscopic measurements.

The vinyl addition reaction, used to form crosslinked polymers, can be initiated by a free-radical generating system. Free radicals can be formed through variety of mechanisms including thermal decomposition and photochemical activation. There are many examples of thermal initiators that produce free radicals from peroxides (e.g. benzoyl peroxide), persulfates (e.g. ammonium persulfate), and nitrogen bonds (e.g. azobisisobutyronitrile). Likewise, there are many examples of photochemically activated initiators such as methylene blue and riboflavin. Ammonium persulfate in the presence of N,N,N',N'-Tetramethylethylenediamine (TEMED) is used as a free-radical initiator in the following examples as it is water soluble and suitable for room-temperature reactions. Reagent solutions can be be purified to remove free radical quenching species, such as dissolved oxygen and quinone inhibitors added by the manufacturer as a stabilizer.

The initiator concentration can have a large influence on the overall polymerization reaction rate and physical properties of the copolymer. In general, slow polymerization reactions (greater than 1 hour to gel onset) can be desirable as they promote uniform reactions and long-chain polymers. If there are problems with the scattering particles settling in this time frame, the sample can be gently rotated or stirred in a manner that does not entrap air bubbles.

While the crosslinked gels in the following examples combine one monomer and one crosslinking agent, one skilled in the art will recognize that acceptable covalently-crosslinked gels can also be made via the copolymerization of two or more monomers and/or two or more crosslinking agents with an initiator reagent. Combining one or more crosslinking agents with an initiator reagent without any monomer groups can also produce acceptable gels. Combining one or more monomers with an initiator reagent in the absence of crosslinking agent tends to yield highly viscose fluids, which can be less desirable than crosslinked gels. For clarity, the examples that follow produce acceptable gels from a single monomer, crosslinking agent, and an initiator reagent.

The reagent concentrations and reaction conditions can have a large influence on the optical and physical properties of the resulting polymer. Acceptable gels have been made with monomer concentrations ranging from 2 to 18% (w/w), provided the monomer is soluble at the upper limit. Acceptable gels have been made with monomer:crosslinker ratios of 10:1 to 100:1 (w/w) provided the crosslinking agent is soluble at the upper limit. In general, high monomer and crosslinker concentrations give more rigid gels. The tradeoff is that the concentrated gels will have stronger absorbance features, which may not meet the optical similarity requirements. Another concern is that concentrated gels may undergo syneresis, where the polymer and water separate into two phases.

Example 25 ml samples of polyacrylamide gel prepared in a vial for further optical and mechanical testing. Unless otherwise noted, the reagent stock solutions are in phosphate buffered saline (PBS), which was prepared from Sigma electrophoresis reagent at the standard 10× dilution, using constituents such as the following:

2% (weight/volume) N,N'-methylenebisacrylamide
25% (weight/volume) acrylamide
0.05% (weight/volume) ammonium persulfate
0.05% (volume/volume) TEMED Scattering bead and analyte solution with appropriate level for the desired optical properties in the final gel (typically prepared for a 2.5 dilution to final gel volume).

Ammonium persulfate solutions should be made fresh each day; stock solutions of the other reagents can be stored in a fridge for up to a week. Unless otherwise noted, the reagents should be prepared and reacted at 25 C.

Preparation

Gently degas the solutions under vacuum for 10 minutes.
Form the gel precursor by adding all the reagents in Table 8, except ammonium persulfate, to a 40 ml vial with a septum lid with gently stirring.
Seal the vial and sparge the gel precursor with nitrogen bubbles for 15 minutes. An easy method is to introduce the gas via a septum-penetrating needle inserted to the bottom of the vial with a second needle in the headspace to allow the gas to exit. At the end of sparging, the needles can be completely removed, or if it doesn't interfere with subsequent steps, the gas-delivering needle can be withdrawn into the headspace to maintain a positive nitrogen atmosphere.
Ammonium persulfate can be added through the septum with a hypodermic syringe and the vial is gently stirred to initiate the polymerization reaction.
If no gel forms after 24 hours, the initiator concentration is too low. If the gel onset is observed in less than 10 minutes, or the gels are cloudy, the initiator concentration is too high. The optimum initiator concentration, which produces gels in 1 to 24 hours, will depend on reagent purity, dissolved oxygen levels and other experimental factors.

Example Preparation of HEC OSRS

As an example, an OSRS comprising HEC can be prepared according to the following. Note that the order and technique can be important in realizing an OSRS with the desired properties.

Associated supplies: water; Polystyrene microspheres (Bangs Laboratories, with diameters of 298 nm, 930 nm, 3530 nm, and 6300 nm (2% DVB)); Sodium dodecyl sulfate (sodium lauryl sulfate, J. T. Baker L050-07, practical grade, 95% SDS); Hydroxyethyl cellulose (Hercules' Natrosol 250LR, 90000 MW); 60 mL BD syringe.

Associated equipment: analytical balance; beakers; stirring equipment (magnetic, paddle); Sorvall RC-5B centrifuge and GSA rotor; tools to modify syringe (drill press, band saw, cutting tool); spatula.

Steps in the preparation:
1. If needed, design and prepare aqueous analyte sample for later mixture. Keep 50 mL beaker covered with Parafilm.
2. Add sodium dodecyl sulfate to water or sample and stir until dissolved.
3. Sonicate bead stock solution until beads are dispersed. Measure out and add beads to sample.
4. With increasing stirring rate, add polymer (HEC) onto the side of the vortex of the stirred sample.
5. Stop mixing when solution thickens, after about 5 minutes.
6. Let polymer hydrate at room temperature for 2 to 3 days.
7. If syringe loading is desirable for the intended application, load gel into a 60 mL disposable syringe. Modify syringe for centrifuging, by pinning plunger and cutting off excess syringe. Keep tip of syringe up to keep air at that end.
8. Heat to 80 degrees Celsius then centrifuge for 30 minutes at 3000 rpm (Sorvall GSA rotor, 1464 gravities) to move air bubbles to tip of syringe. Balance with a bead-less sample to monitor bubble migration. Re-heat and re-centrifuge if needed to remove excess air bubbles.
9. Continue cycles of allowing bubbles to expand overnight and re-centrifuging until all air has been moved to the tip of the syringe.
10. If sample will not be used immediately, irradiate for 30 minutes with a 104 Rad Cesium 137 source.
11. If needed, calculate component concentrations in mg/dL.
12. Load into scattering background holder.

Example Preparation of PVA OSRS

As an example, an OSRS comprising PVA can be prepared according to the following. Note that the order and technique can be important in realizing an OSRS with the desired properties.

Associated supplies: water; Polystyrene microspheres (Bangs Laboratories, with diameters of 298 nm, 930 nm, 3530 nm, 6300 nm (2% DVB)); Polyvinyl alcohol (DuPont's Elvanol 70-03, 5000 to 8000 MW, 98% hydrolyzed); Borax (Sigma B-3545); 60 mL BD syringe.

TABLE 8

| Example | Acrylamide (mL) | Bisacrylamide (mL) | TEMED (mL) | Scattering Solution (mL) | PBS (mL) | Ammonium Persulfalte (mL) |
|---------|-----------------|--------------------|------------|--------------------------|----------|---------------------------|
| 1 | 4 | 0.75 | 1.0 | 10 | 10.25 | 1.0 |
| 2 | 4 | 3.0 | 1.0 | 10 | 8.0 | 1.0 |
| 3 | 8 | 1.5 | 0.7 | 10 | 5.5 | 0.7 |
| 4 | 8 | 6.0 | 0.7 | 10 | 1.0 | 0.7 |

Associated equipment: analytical balance; beaker ; heating and stirring equipment (magnetic, paddle); Sorvall RC-5B centrifuge and GSA rotor; tools to modify syringe (drill press, band saw, cutting tool); spatula.

Steps in the preparation:
1. If needed, design and prepare aqueous analyte sample for later mixture. Keep 50 mL beaker covered with Parafilm.
2. Sonicate bead stock solution until beads are dispersed. Measure out and add beads to water or sample.
3. Add polymer (PVA) to vortex of stirred sample and heat to 80 degrees Celsius. Continue to stir at 80 degrees Celsius for 2 hours to dissolve the polymer.

4. Prepare crosslinker solution by stirring borax in water at 80 degrees Celsius for 5 minutes to dissolve borax.
5. To prepare gel, pour warm polymer solution (80 degrees Celsius) into beaker or plastic bag, then add warm (80 degrees Celsius) crosslinking solution.
6. Quickly stir or knead to prepare a uniform sample.
7. If syringe loading is desirable for the intended application, load gel into 60 mL disposable syringe and modify syringe for centrifuging, by pinning plunger and cutting off excess syringe. Keep tip of syringe up to keep air at that end.
8. Reheat to 80 degrees Celsius then centrifuge for 30 minutes at 3000 rpm (Sorvall GSA rotor, 1464 gravities) to move air bubbles to tip of syringe. Balance with a bead-less sample to monitor bubble migration. Re-heat and re-centrifuge when residual bubbles have had time to expand, after about 8 hours.
9. Continue cycles of allowing bubbles to expand overnight and re-centrifuging until all air has been moved to the tip of the syringe.
10. If sample will not be used immediately, irradiate for 30 minutes with a 104 rad Cesium 137 source.
10. Measure gel density by difference, and calculate component concentrations in mg/dL.
12. Load into scattering background holder.

Results From Example OSRS

Reference gel formulations as shown in Table 9 were prepared. They were measured consistent with the methodology described herein, resulting in reference absorbance spectra similar to that shown in FIG. 6.

TABLE 9

| | A mg/dL | B mg/dL | C mg/dL | D mg/dL | E mg/dL |
|---|---|---|---|---|---|
| PS 0.298 μm | — | — | — | 172.7 | 199.4 |
| PS 0.93 μm | 1619 | 374 | 419 | 937.6 | 915.8 |
| PS 2 μm | — | — | 135 | — | — |
| PS 3.53 μm | — | — | 71 | 314.6 | 92.5 |
| PS 6.3 μm | — | 90 | — | 304.5 | 644.1 |
| HEC | 31886 | 33036 | 32932 | 31902.8 | 35425.8 |
| SLS | 1086 | 1097 | 1119 | 1028.7 | 3998.2 |
| H$_2$0 | 77024 | 77369 | 77291 | 75281.7 | 70004.8 |

Other OSRS Characteristics

The spectral characteristics of an OSRS according to the present invention can be affected by control of physical characteristics of the OSRS; e.g., by controlling the temperature, the pH, or the ionic content. Further, specific materials can be included in an OSRS to match the spectral characteristics of specific tissues; e.g., proteins, lipids, or other materials can be included in an OSRS according to the present invention.

Those skilled in the art will recognize that the present invention may be manifested in a variety of forms other than the specific embodiments described and contemplated herein. Accordingly, departures in form and detail may be made without departing from the scope and spirit of the present invention as described in the appended claims.

What we claim is:

1. A method of characterizing the performance of an infrared spectroscopic system, comprising:
   a. providing a reference sample comprising a gelling agent; a scattering agent that scatters infrared energy; and water;
   b. using the infrared spectroscopic system to measure the response of the reference sample to incident radiation;
   c. characterizing the performance of the infrared spectroscopic system from a comparison of the measured response with a response expected from the known properties of the reference sample.

2. A method as in claim 1, wherein the scattering agent comprises a mesh, a filament, or a combination thereof.

3. A method as in claim 1, wherein the gelling agent comprises hydroxyethylcellulose.

4. A method as in claim 3, wherein the hydroxyethylcellulose (HEC) and the water are present at a ratio of 30 weight % HEC to 70 weight % water.

5. A method as in claim 1, wherein the gelling agent comprises polyvinyl alcohol.

6. A method as in claim 5, wherein the polyvinyl alcohol (PVA) and the water are present at a ratio of 30 weight % PVA to 70 weight % water.

7. A method as in claim 1, wherein the gelling agent comprises an initiator and a crosslinking agent that contains a plurality of vinyl groups.

8. A method as in claim 7, wherein the crosslinking agent comprises N,N'-methylenebisacrylamide, ethylene glycol dimethacrylate, bisacrylamide, or a combination thereof.

9. A method as in claim 7, wherein the initiator comprises a peroxide, benzoyl peroxide, a persulfate, ammonium persulfate, azobisisobutyronitrile, a photochemically activated initiator, methylene blue, riboflavin, ammonium persulfate in the presence of N,N,N',N'-Tetramethylethylenediamine, or a combination thereof.

10. A method as in claim 7, wherein the gelling agent further comprises a monomer that contains a vinyl group.

11. A method as in claim 10, wherein the monomer comprises acrylamide, 2-hydroxyethyl methacrylate, poly (ethylene glycol) methacrylate, 1-vinyl-2-pyrrolidinone, or a combination thereof.

12. A method as in claim 1, wherein the reference sample further comprises an analyte.

13. A method as in claim 1, wherein the reference sample further comprises a protein, a lipid, or a combination thereof.

14. A method as in claim 1, wherein the reference sample further comprises a temperature control agent, a pH control agent, an ionic control agent, or a combination thereof.

15. A method as in claim 1, wherein the scattering agent comprises a first plurality of scattering particles having a first scattering characteristic and a second plurality of scattering particles having a second scattering characteristic, wherein the first scattering characteristic is different than the second scattering characteristic.

16. A method as in claim 1, wherein the scattering agent comprises particles of at least two different sizes.

17. A method as in claim 1, wherein the scattering agent comprises particles of at least two different shapes.

18. A method as in claim 1, wherein the scattering agent comprises particles of at least two different refractive indices.

19. A method as in claim 1, wherein the scattering agent comprises polystyrene particles.

20. A method as in claim 19, wherein the polystyrene particles have a diameter chosen from the group consisting of: 0.2 to 4 μm; 0.14 to 0.35 μm; 0.3 μm; 0.8 to 1 μm; 0.9 to 0.95 μm; 0.93 μm; 5 to 6 μm; 4 to 5 μm; 5.3 to 5.7 μm; 5.5 μm; 6 to 7 μm; 6.2 to 6.5 μm; and 6.3 μm.

21. A method as in claim 19, where the polystyrene particles have a diameter of 0.8 to 1.0 μm, and wherein the polystyrene particles are present at a concentration chosen from the group consisting of: 1400 to 1800 mg/dL; and 1600 mg/dL.

22. A method as in claim 21, wherein the reference sample comprises:
 a. 1,400 to 1,800 mg/dL polystyrene beads;
 b. 500 to 1,500 mg/dL viscosity control agent; and
 c. 75,000 to 80,000 mg/dL water.

23. A method as in claim 22, wherein the reference sample has a spectral absorbance peak at a wavelength of 5,200 cm-1 and 6,900 cm-1.

24. A method as in claim 21, wherein the reference sample comprises:
 a. 1,600 mg/dL polystyrene beads;
 b. 1000 mg/dL viscosity control agent; and
 c. 77,000 mg/dL water.

25. A method as in claim 19, wherein the polystyrene particles comprise a first group of polystyrene particles having a first diameter and a second group of polystyrene particles having a second diameter wherein the first diameter is different than the second diameter.

26. A method as in claim 25, further comprising a third group of polystyrene particles having a third diameter wherein the third diameter is different than the first and the second diameter.

27. A method as in claim 26, further comprising a fourth group of polystyrene particles having a fourth diameter wherein the fourth diameter is different from the first, second and third diameter.

28. A method as in claim 27, wherein the first diameter is 0.25 to 0.35 μm, the second diameter is 0.9 to 0.95 μm, the third diameter is 5.3 to 5.7 μm, and the fourth diameter is 6.2 to 6.5 μm.

29. A method as in claim 28, wherein the first diameter is 0.3 μm, the second diameter is 0.93 μm, the third diameter is 5.5 μm and the fourth diameter is 6.3μm.

30. A method as in claim 28, wherein the reference sample comprises:
 a. 150 to 250 mg/dL of the first group of polystyrene beads;
 b. 900 to 950 mg/dL of the second group of polystyrene beads;
 c. 50 to 350 mg/dL of the third group of polystyrene beads; and
 d. 250 to 700 mg/dL of the fourth group of polystyrene beads.

31. A method as in claim 30, wherein the reference comprises:
 a. 1,300 to 2,300 mg/dL polystyrene beads;
 b. 1,000 to 4,000 mg/dL viscosity control agent; and
 c. 70,000 to 80,000 mg/dL water.

32. A method as in claim 31, wherein the reference sample has a spectral absorbance peak at a wavelength of 5,200 cm-1 and 6,900 cm-1.

33. A method as in claim 28, wherein the reference sample comprises:
 a. 170 mg/dL of the first group of polystyrene beads;
 b. 940 mg/dL of the second group of polystyrene beads;
 c. 310 mg/dL of the third group of polystyrene beads; and
 d. 300 mg/dL of the fourth group of polystyrene beads.

34. A method as in claim 33, wherein the reference samole comprises:
 a. 1,700 mg/dL polystyrene beads;
 b. 1,000 mg/dL viscosity control agent; and
 c. 75,000 mg/dL water.

35. A method as in claim 33, wherein the reference sample comprises:
 a. 1,850 mg/dL polystyrene beads;
 b. 4,000 mg/dL viscosity control agent; and
 c. 70,000 mg/dL water.

36. A method as in claim 28, wherein the reference sample comprises:
 a. 200 mg/dL of the first group of polystyrene beads;
 b. 920 mg/dL of the second group of polystyrene beads;
 c. 90 mg/dL of the third group of polystyrene beads; and
 d. 640 mg/dL of the fourth group of polystyrene beads.

37. A method as in claim 1, wherein the reference sample further comprises a viscosity control agent.

38. A method as in claim 37, wherein the viscosity control agent comprises sodium lauryl sulfate, ammonium lauryl sulfate, or combinations thereof.

39. A method as in claim 37, wherein the viscosity control agent comprises sodium lauryl sulfate, ammonium lauryl sulfate, a latex emulsion, a cellulosic water-soluble polymer, a water-soluble resin, a natural gum, a preservative, a surfactant, a defoamer, a plasticizer, an organic solvent, or combinations thereof.

40. A method as in claim 37, wherein the reference sample comprises:
 a. 30,000–40,000 mg/dL gelling agent;
 b. 1,000–2,500 mg/dL polystyrene particles;
 c. 100–5.000 mg/dL viscosity control agent; and
 d. 60,000–85,000 mg/dL water.

41. A method as in claim 1, wherein the reference sample has spectral absorbance peaks at wavelengths of about 5,200 cm-1 and about 6,900 cm-1.

42. A method as in claim 1, wherein the gelling agent contains a plurality of vinyl groups; and wherein the reference sample further comprises an initiator.

43. A method as in claim 42, wherein the gelling agent comprises N,N'-methylenebisacrylamide, ethylene glycol dimethacrylate, bisacrylamide, or a combination thereof.

44. A method as in claim 42, wherein the initiator comprises peroxide, benzoyl peroxide, a persulfate, ammonium persulfate, azobisisobutyronitrile, a photochemically activated initiator, methylene blue, riboflavin, ammonium persulfate in the presence of N,N,N', N'-Tetramethylethylenediamine, or a combination thereof.

45. A method as in claim 42, wherein the reference sample further comprises a monomer that contains a vinyl group.

46. A method as in claim 45, wherein the monomer comprises acrylamide, 2-hydroxyethyl methacrylate, poly(ethylene glycol) methacrylate, 1-vinyl-2-pyrrolidinone, or a combination thereof.

47. A method as in claim 42, wherein the reference sample further comprises an accelerant.

* * * * *